US009956426B2

(12) United States Patent
Punjabi

(10) Patent No.: US 9,956,426 B2
(45) Date of Patent: May 1, 2018

(54) UPCONVERTING NANOPARTICLES

(71) Applicant: Amol Punjabi, Northborough, MA (US)

(72) Inventor: Amol Punjabi, Northborough, MA (US)

(*) Notice: Subject to any disclaimer, the term of this patent is extended or adjusted under 35 U.S.C. 154(b) by 0 days. days.

(21) Appl. No.: 14/632,752

(22) Filed: Feb. 26, 2015

(65) Prior Publication Data
US 2016/0250332 A1   Sep. 1, 2016

(51) Int. Cl.
| A61K 41/00 | (2006.01) |
| A61N 5/06 | (2006.01) |
| A61K 47/48 | (2006.01) |
| C09K 11/02 | (2006.01) |
| C09K 11/77 | (2006.01) |
| A61K 47/69 | (2017.01) |

(52) U.S. Cl.
CPC ............ *A61N 5/062* (2013.01); *A61K 41/008* (2013.01); *A61K 41/0061* (2013.01); *A61K 47/6923* (2017.08); *A61K 47/6929* (2017.08); *C09K 11/025* (2013.01); *C09K 11/7773* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| 8,323,694 | B2 | 12/2012 | Hainfield | |
| 8,546,447 | B2 | 10/2013 | Godal et al. | |
| 9,333,271 | B2 * | 5/2016 | Han | A61K 49/0052 |
| 2011/0021970 | A1 * | 1/2011 | Vo-Dinh | A61K 49/0039 604/20 |
| 2011/0223105 | A1 * | 9/2011 | Eriksson | A61K 31/27 424/9.1 |
| 2013/0224071 | A1 * | 8/2013 | Bernstein | A61L 2/081 422/24 |
| 2014/0056817 | A1 * | 2/2014 | Yuasa | A61K 41/0061 424/9.6 |

FOREIGN PATENT DOCUMENTS

| WO | WO2010024775 A1 | 3/2010 |
| WO | WO2010142456 A1 | 12/2010 |
| WO | WO2012039685 A1 | 3/2012 |
| WO | WO2013016696 A1 | 1/2013 |
| WO | WO2013087734 A2 | 6/2013 |
| WO | WO2013181076 A1 | 12/2013 |
| WO | WO2014116631 A1 | 7/2014 |

OTHER PUBLICATIONS

Abdelaal et al., American Journal of Polymer Science (2012), vol. 2, No. 4, pp. 73-78.*
S.M. Amini et al., IET Nanobiotechnol, 2013, 7, 151-156.
P. Bilski, et al., Free Radical Biol. Med., 2002, 33, 938-946.
M. Bottini et al., J. Nanosci. Nanotechnol., 2014, 14, 98-114 (abstract).
A. Borgatti-Jeffreys; et al., Am. J. Vet. Res., 2007, 68, 399-404.
J.-C. Boyer, et al., Nanoscale, 2010, 2, 1417-1419.
D. K. Chatterjee, et al., Adv. Drug Del. Rev., 2008, 60, 1627-1637.
D. K. Chatterjee, et al., Nanomedicine, 2008, 3, 73-82 (abstract).
G. Chen, et al., Chem. Rev,. 2014, 114, 5161-5214.
G. Chen, et al., ACS Nano, 2012, 6, 8280-8287.
S. Collaud, et al., Current Medicinal Chemistry—Anti-Cancer Agents, 2004, 4, 301-316 (abstract).
Y. Dai, et al., Biomaterials, 2012, 33, 8704-8713.
Y. Ding, et al., Nanoscale, 2013, 5, 11928-11932.
D. E. J. G. J. Dolmans, et al., Nat. Rev. Cancer, 2003, 3, 380-387.
T. J. Dougherty, et al., J. Natl. Cancer Inst., 1998, 90, 889-905.
M. B. Ericson, et al., Ther. Clin. Risk Manag. 2008, 4, 1-9.
W. Feng, et al., Adv. Mater., 2013, 25, 5287-5303.
M. Haase, et al., Angew. Chem. Int. Ed. Engl., 2011, 50, 5808-5829.
Z. Huang, Technol. Cancer Res. Treat., 2005, 4, 283-293.
N.M. Idris, et al., Nat. Med., 2012, 18, 1580-1585.
H. Kato; et al., Lung Cancer, 2003, 42, 103-111.
G. B. Kharkwal et al., Lasers Surg. Med., 2011, 43(7), 755-767.
K. W. Krämer, et al., Chem. Mater., 2004, 16, 1244-1251.
K. Liu, et al., ACS Nano, 2012, 6, 4054-4062.
J. F. Lovell, et al., Chem. Rev., 2010, 110, 2839-2857.
I. J. Macdonald, et al., J. Porphyrins Phthalocyanines, 2001, 5, 105-129.
V. Ntziachristos, et al., Eur. Radiol., 2003, 13, 195-208.
M. A. Oar, et al., Chem. Mater., 2005, 17, 2267-2275.
M.K. Oo et al., NSTI-Nanotech, 2008, 2, 12-15.
Q. Peng, et al., Photochem. Photobiol., 1997, 65, 235-251.
Q. Peng, et al., Cancer, 1997, 79, 2282-2308.
W. Piao et al., Angew. Chem. Int. Ed. 2013, 52, 13028-13032.
A. Punjabi, et al., ACS Nano, 2014, 8(10), 10621-10630 and supplementary material.
H. S. Qian, et al., Small, 2009, 5, 2285-2290.
X.-F. Qiao, et al., Nanoscale, 2012, 4, 4611-4623.
J. Shan, et al., Adv. Funct. Mater., 2011, 21, 2488-2495.
J. Shen, et al., Small, 2013, 9, 3213-3217.
X. Teng, et al., J. Am. Chem. Soc., 2012, 134, 8340-8343.
G. Tian, et al., Small, 2013, 9, 1929-1938.
G. Tian, et al., Adv. Mater,. 2012, 24, 1226-1231.
C. Wang, et al., Biomaterials, 2011, 32, 1110-1120 (abstract).
C. Wang, et al., Biomaterials 2011, 32, 6145-6154.
F. Wang, et al., Analyst, 2010, 135, 1839-1854.
F. Wang, et al., Chem. Soc. Rev., 2009, 38, 976-989.
F. Wang, et al., Nat. Mater., 2011, 10, 968-973.
F. Wang, et al., J. Am. Chem. Soc., 2008, 130, 5642-5643.
S. Wang, et al., J. Mater. Chem., 2004, 14, 487-493.
Y.-F. Wang, et al., Chemistry—A European Journal, 2012, 18, 5558-5564.
J. Wang, et al., Nat. Mater., 2014, 13, 157-162.
H. L. Wen, et al., Angew. Chem., Int. Ed. 2013, 52, 13419-13423 (abstract).
L. Zhao, et al.,Theranostics, 2013, 3, 249-257.

* cited by examiner

Primary Examiner — Hasan Ahmed
Assistant Examiner — Frank Choi
(74) Attorney, Agent, or Firm — Fish & Richardson P.C.

(57) ABSTRACT

Provided herein are lanthanide-containing upconverting nanoparticles, methods of their preparation, compositions, and methods of using the same. The polymers and compositions provided herein may be used, for example, in photodynamic therapy.

18 Claims, 16 Drawing Sheets

UPCONVERTING NANOPARTICLES

TECHNICAL FIELD

This invention relates to lanthanide up-conversion nanoparticles and their use, e.g., for photodynamic therapy.

BACKGROUND

The inherent limitations of normal fluorescence have encouraged the development of alternative techniques and compounds. There are at least two such limitations on using normal fluorescent molecules for biological imaging and therapy. First, cells have many fluorescent molecules of their own, leading to unwanted background fluorescence that can be particularly problematic in sensitive experiments such as single-molecule imaging. Second, the intense light typically used by microscopes to excite fluorescent molecules can damage cells, especially light at the ultraviolet (UV) and blue end of the visible spectrum. Photo damage may also occur indirectly, if the excited state of a fluorescent molecule reacts with a nearby molecule instead of emitting fluorescence.

Photodynamic therapy (PDT) is a favorable cancer treatment modality due to its minimally invasive nature, leading to fewer side effects than chemotherapy and less damage to marginal tissue. Photodynamic therapy is a treatment that uses a non-toxic photosensitive compound, called a photosensitizer or photosensitizing agent, and a particular type of light. When photosensitizers are exposed to a specific wavelength of light, they produce a form of oxygen that kills nearby cells. In air and tissue, molecular oxygen occurs in a triplet state, whereas most other molecules are in a singlet state. Reactions between these are forbidden by quantum mechanics, thus oxygen is relatively non-reactive at physiological conditions. A photosensitizer is a chemical compound that can be promoted to an excited state upon absorption light and undergo intersystem crossing with oxygen to produce singlet oxygen. This species rapidly reacts with organic compounds it encounters, and is thus highly cytotoxic.

Each photosensitizer is activated by light of a specific wavelength. The photosensitizers used in conventional photodynamic therapy are mostly activated by visible light, which cannot pass through thick tissue. The application of these visible light photosensitizers is limited to treating tumors on or just under the skin or on the lining of internal organs or cavities and is less effective when treating large tumors deep under the skin. Treatment methods involve directly activating a photosensitizer to generate singlet oxygen that is toxic to cancer cells under irradiation with light in the visible region. Of the colors in this spectrum, longer wavelength red (i.e., 620-670 nm) light is preferred by the majority of photosensitizers in clinical practice due to its improved tissue penetration compared to shorter wavelength light. The use of near-infrared light in photodynamic therapy can afford greater penetration depths than that of visible light because the absorbance for most biomolecules reaches a minimum in the near-infrared light window (having a wavelength of 700-1100 nm).

Upconverting nanoparticles (UCNPs) are a promising new generation of agents for bio imaging and photodynamic therapy. Normal fluorescence converts higher-energy (i.e., shorter wavelength) light to lower-energy (i.e., longer wavelength) emitted light. Upconversion luminescence, on the other hand, refers to an anti-Stokes type process in which the sequential absorption of two or more low-energy (i.e., longer wavelength) photons by a nanoparticle, is followed by the emission of a single higher-energy (i.e., shorter wavelength) photon. Applications of UCNPs include bio sensing, chemical sensing, in vivo imaging, drug delivery, photodynamic therapy and photoactivation.

Lanthanide-doped UCNPs are dilute guest—host systems where trivalent lanthanide ions are dispersed in an appropriate dielectric host lattice that typically has a dimension of less than about 100 nm. Lanthanide-doped UCNPs have been developed that are excited by tissue-penetrable near-infrared light and have emissions ranging from visible to ultraviolet light. Lanthanide ion ($Ln^{3+}$) containing UCNPs are able to absorb near-infrared (NIR) photons and convert such low energy excitation into shorter wavelength emissions. Haase, et al., *Angew. Chem. Mt. Ed.*, 2011 50, 5808. Due to the long lived energy levels of lanthanide ions, the intensity of the anti-Stokes luminescence of such UCNPs is more potent compared with that of conventional synthetic dyes. UCNPs have been developed that are excited by tissue-penetrable near-infrared light (e.g., 980 nm) and have emissions ranging from visible to ultraviolet.

Lanthanide-doped upconverting nanoparticles are particularly useful for use in photodynamic therapy, an emerging treatment modality for a variety of diseases. In contrast to other photosensitizers such as photofrin, low cost 5-aminolevulinic acid (5-ALA) has unique advantages due to its hydrophilicity, higher selectivity in cancerous cells, and reduced concomitant photosensitivity, leading to minimal trauma in surrounding tissue. 5-ALA converts to the photosensitizer protoporphyrin IX (PpIX) via a heme biosynthesis pathway. Because this occurs to a greater extent in tumors than in non-cancerous cells due to the down regulation of the enzyme ferrochelatase (a PpIX degrading factor) in cancerous cells, PpIX selectively targets cancerous cells over non-cancerous cells. Peng, et al., 5-Aminolevulinic Acid-Based Photodynamic Therapy, *Cancer,* 1997, 79, 2282. Under irradiation with red light, PpIX converts triplet oxygen into singlet oxygen, inducing cell death. Despite much progress in its clinical use, ALA's application is limited because while red light offers the maximum tissue penetration of the wavelengths in PpIX's activation spectrum, it is still absorbed or dispersed by common components of tissue, rendering deep-tissue (>1 cm) photodynamic therapy challenging.

SUMMARY

The present disclosure provides novel upconverting luminescence materials (e.g., UCNPs) and methods that have enhanced upconverting luminescence efficiency that can be useful, e.g., for the treatment of deep tumors.

The present disclosure provides a nanoparticle comprising a rare earth metal fluoride composition according to the formula $M^1M^2F_4$ comprising lanthanide ions, wherein $M^1$ is the alkali metal, $M^2$ is the rare earth, and wherein the composition comprises: ytterbium in an amount from about 70 mol % to about 99 mol % of the rare earth present in the composition; erbium in an amount from about 0.1 mol % to about 10 mol % of the rare earth present in the composition; and yttrium in an amount from about 0 mol % to about 30 mol % of the rare earth present in the composition.

In some embodiments, the alkali metal is sodium.

In some embodiments, the nanoparticle comprises: ytterbium in an amount of about 98 mol % of the rare earth present in the composition; and erbium in an amount of about 2 mol % of the rare earth present in the composition.

In some embodiments, the nanoparticle comprises: ytterbium in an amount of about 70 to 90 mol % of the rare earth present in the composition; erbium in an amount of about 1 to 5 mol % of the rare earth present in the composition; and yttrium in an amount from about 10 to 30 mol % of the rare earth present in the composition.

In some embodiments, the nanoparticle comprises: ytterbium in an amount of about 80 mol % of the rare earth present in the composition; erbium in an amount of about 2 mol % of the rare earth present in the composition; and yttrium in an amount of about 18 mol % of the rare earth present in the composition.

In some embodiments, the nanoparticle is included in an aqueous composition.

In some embodiments, the nanoparticle comprises a coating or shell comprising calcium fluoride.

In some embodiments, the nanoparticle comprises a photosensitizer, or precursor thereof.

In some embodiments, the photosensitizer or precursor thereof is covalently attached to the nanoparticle.

In some embodiments, the photosensitizer or precursor thereof is 5-aminolevulinic acid.

In some embodiments, the nanoparticle comprises: ytterbium in an amount of about 80 mol % of the rare earth present in the composition; erbium in an amount of about 2 mol % of the rare earth present in the composition; and yttrium in an amount of about 18 mol % of the rare earth present in the composition; a coating comprising calcium fluoride; polyacrylic acid; and 5-aminolevulinic acid conjugated via a hydrazone linkage to the polyacrylic acid.

In some embodiments, the disclosure provides a method of photodynamic therapy to treat, e.g., a skin condition or a tumor in a subject in need of such treatment comprising: administering to the subject an effective amount of the nanoparticle as described herein, administering to the subject an effective amount of a photosensitizer or precursor thereof; and subsequently administering to the subject an effective amount of infra-red radiation. In some such embodiments, the nanoparticle comprises the photosensitizer or precursor thereof. In some embodiments, the photosensitizer or precursor thereof is covalently attached to the nanoparticle. In some embodiments, the photosensitizer or precursor thereof is 5-aminolevulinic acid.

A method of preparing an upconverting nanoparticle is provided, wherein the method comprises reacting in a reaction mixture rare earth trifluoroacetates and sodium trifluoroacetate under conditions sufficient to form a sodium rare earth tetrafluoride, wherein the rare earth trifluoroacetates are selected from the group consisting of: ytterbium trifluoroacetate in an amount from about 70 mol % to about 99 mol % of the rare earth trifluoroacetates present in the reaction mixture; erbium trifluoroacetate in an amount from about 0.1 mol % to about 10 mol % of the rare earth trifluoroacetates present in the reaction mixture; and yttrium trifluoroacetate in an amount from about 0 mol % to about 30 mol % of the rare earth trifluoroacetates present in the reaction mixture. In some embodiments, the rare earth trifluoroacetates present in the mixture comprise, consist essentially of, or consist of ytterbium trifluoroacetate, erbium trifluoroacetate and (optionally) yttrium trifluoroacetates, wherein the rare earth trifluoroacetates are present in a ratio to provide the ratio desired in the nanoparticle. In some embodiments, the rare earth trifluoroacetates comprise, consist essentially of or consist of ytterbium trifluoroacetate in an amount of about 80 mol % of the rare earth trifluoroacetates present in the reaction mixture; erbium trifluoroacetate in an amount of about 2 mol % of the rare earth trifluoroacetates present in the reaction mixture; and yttrium trifluoroacetate in an amount of about 18 mol % of the rare earth trifluoroacetates present in the reaction mixture. Also provided are nanoparticles prepared according to such methods.

Despite some progress, few studies have been targeted towards the activation of FDA-approved drugs and/or prodrugs by upconverting nanoparticles, particularly by clinically preferred red light. Moreover, the approaches to enhance red-emissions in UCNPs are still limited and there has been no demonstration that photodynamic therapy can work at depths beyond 1 cm. Hexagonal phase core/shell upconverting nanoparticles with core doping concentrations of 20%-30% ytterbium and 2% erbium are have been investigated as potential agents for photodynamic therapy. Chatterjee, et al., Upconverting Nanoparticles As Nanotransducers For Photodynamic Therapy In Cancer Cells, *Nanomedicine*, 2008, 1, 73. Other attempts to produce upconverting nanoparticles with greater upconversion efficiency have also met with limited success. Wang, et al., Drug Delivery With Upconversion Nanoparticles For Multi-Functional Targeted Cancer Cell Imaging And Therapy, *Biomaterials*, 2011, 32, 1110. Teng, et al., *J. Am. Chem. Soc.*, 2012, 134, 8340.

Another drawback of upconverting nanoparticles is the presence of heavy metals in the compositions which have the potential for ion leakage, potentially leading to dangerous biological toxicity. Wang et al., *Chemistry—A European Journal*, 2012, 18, 5558 (2012). As a result, there is an emerging demand to engineer UCNPs with enhanced near infra-red-to-red upconversion and better biocompatibility with respect to effective phototherapy in a deep-tissue environment.

Although methods and materials similar or equivalent to those described herein can be used in the practice or testing of the present invention, suitable methods and materials are described below. All publications, patent applications, patents, and other references mentioned herein are incorporated by reference in their entirety. Where the first page number of a reference is given in a citation, it is to be understood that reference is being made to the entire article cited. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
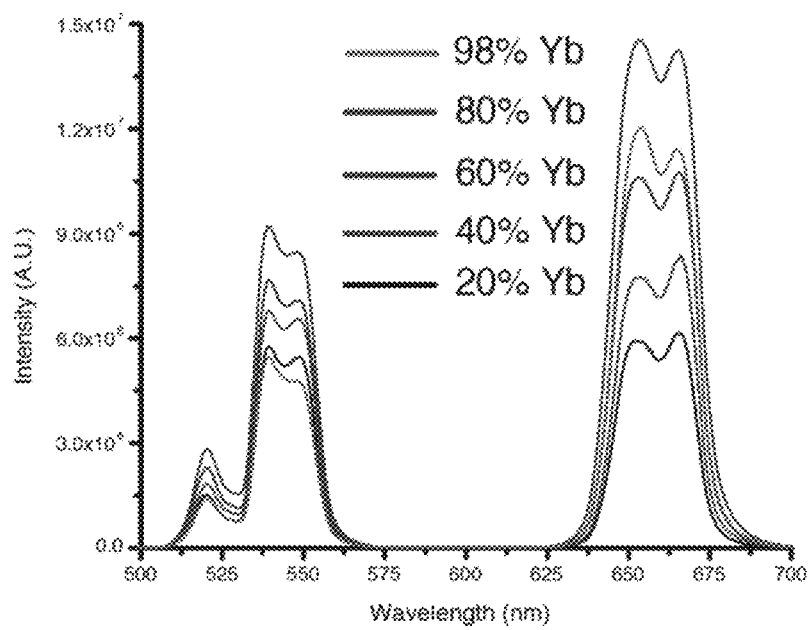
FIG. 1A: Emission spectra under CW 980 nm 1 W/cm$^2$ excitation of α-NaYF$_4$:Yb,Er@CaF$_2$ UCNPs with different Yb-levels from 20 to 98%—increased levels of Yb lead to increased fluorescence.

The present disclosure provides lanthanide-doped upconverting nanoparticles with enhanced near infrared to red light outcome and better biocompatibility with respect to effective phototherapy in a deep-tissue environment.

The current application provides lanthanide-doped upconverting nanoparticles that exhibit properties well suited for use in photodynamic therapy. With the advent of nanotechnology, lanthanide-doped upconverting nanoparticles (Ln-doped UCNP) have been developed that are excited by tissue-penetrable near infrared light (e.g., having a wavelength of around 980 nm) and have emissions ranging from visible to ultraviolet, equipping them to be a promising transducer for triggering deep-tissue photodynamic therapy.

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The term "alkali metal" refers to a metal of group 1 (group IA) of the periodic table, including lithium, sodium, potassium and cesium.

The term "infra-red" refers to invisible electromagnetic radiation with longer wavelength than visible light, having wavelength in the range from about 700 nm to about 1 mm.

The term "lanthanide" refers to a chemical element with an atomic number from 57 through 71 (atomic numbers 57 through 71, from lanthanum through lutetium).

The term "rare earth" refers to a chemical element that is a lanthanide, or scandium or yttrium.

The term "nanoparticle" as used herein refers to a particle having a size from about 1 nm to about 1000 nm.

The term "nanoparticle size" as used herein refers to the median size in a distribution of nanoparticles. The median size is determined from the average linear dimension of individual nanoparticles, for example, the diameter of a spherical nanoparticle. Size may be determined by any number of methods in the art, including dynamic light scattering and transmission electron microscopy techniques.

At various places in the present specification, certain features of chemical compounds are disclosed in groups or in ranges. It is specifically intended that such a disclosure include each and every individual sub-combination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

At various places in the present disclosure, variables defining divalent linking groups are described. It is specifically intended that each linking substituent include both the forward and backward forms of the linking group. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methylpropan-1,3-diyl and the like.

The term "amino" refers to a group of Formula —NH$_2$.

The term "carbonyl", employed alone or in combination with other terms, refers to a —C(=O)— group, which also may be written as C(O).

The terms "halo" or "halogen", used alone or in combination with other terms, refers to fluoro, chloro, bromo and iodo. In some embodiments, "halo" refers to a halogen atom selected from F, Cl, or Br. In some embodiments, halo is F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CCl$_3$, CHCl$_2$, C$_2$Cl$_5$ and the like. In some embodiments, the haloalkyl group is a fluoroalkyl group.

The term "heteroalkylene" refers to an alkylene group wherein one or more of the carbon atoms have been replaced by a heteroatom. The term "$C_{n-m}$ heteroalkylene", employed alone or in combination with other terms, refers to a heteroalkylene group containing from n to m carbon atoms. The heteroatoms may be independently selected from the group consisting of O, N and S. A divalent heteroatom (e.g., O or S) replaces a methylene group of the alkylene —CH$_2$—, and a trivalent heteroatom (e.g., N) replaces a methine group. A sulfur atom can be oxidized to a sulfoxide or sulfone group. Examples are divalent straight hydrocarbon groups consisting of methylene groups, —O— atoms and —NH— and —NMe-groups, such as, —CH$_2$O—, —CH$_2$CH$_2$O—, —CH$_2$CH$_2$OCH$_2$—. It is understood that in the compounds described herein, the number and position of heteroatoms in a heteroalkylene group is selected to provide a stable compound. Thus, a heteroalkene group typically does not contain two heteroatoms connected to each other within a chain, and typically includes at least two carbon atoms separating each heteroatom. The $C_{n-m}$ heteroalkylene groups include $C_{1-6}$ heteroalkylene and $C_{1-3}$ heteroalkylene.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

Abbreviations

The following abbreviations and symbols may be used in the present disclosure: ATR (attenuated total reflectance); AcOH (acetic acid); 5-ALA or ALA (5-aminolevulinic acid or 5-amino-4-oxo-pentanoic acid); aq. (aqueous); atm. (atmosphere(s)); $CaF_2$ (calcium fluoride); CCD (charge coupled device); CW (continuous wave); DCF (2',7'-dichlorofluorescein); DCFDA (2',7'-dichlorofluorescein diacetate); DMF (N,N-dimethylformamide); EDC (1-ethyl-3-(3-dimethylaminopropyl) carbodiimide hydrochloride); Er (erbium); Et (ethyl); $Et_2O$ (diethyl ether); EtOAc (ethyl acetate); EtOH (ethanol); FT-IR (Fourier transform HBSS (Hank's Balanced Salt Solution); infra-red spectroscopy); g (gram(s)); h (hour(s)); HCl (hydrochloric acid/hydrogen chloride/hydrochloride); HPLC (high performance liquid chromatography) IPA (isopropyl alcohol); IR (infra-red); Ln (lanthanide or rare earth); Me (methyl); MeCN (acetonitrile); MeOH (methanol); mg (milligram(s)); min. (minutes(s)); mL (milliliter(s)); mm (millimeter(s)); mmol (millimole(s)); mol (mole(s)); mol % (mole percent); MTT (3-(4,5-dimethylthiazol-2-yl)-2,5-diphenyltetrazolium bromide); N (normal); Na (sodium); $NaYF_4$ (sodium yttrium fluoride); nm (nanometer(s)); nM (nanomolar); PBS (phosphate-buffered salinePDT (photodynamic therapy); PEG (poly(ethylene glycol)); PGA (polyglycolic acid); PLA (polylactic acid; PLGA (poly(lactic-co-glycolic acid)); PPG (poly(propylene glycol)); PpIX (protoporphyrin IX); s (second(s)); SMCC (silicified microcrystalline cellulose); sulfo-NHS (N-hydroxysulfosuccinimide (sodium salt)); TEM (transmission electron microscopy); UCNP (upconverting nanoparticle (or, equivalently, upconversion nanoparticle)); UV (ultraviolet); μg (microgram(s)); μL (microliter(s)); μM (micromolar); wt % (weight percent); w/v (weight to volume); Y (yttrium); Yb (ytterbium).

Upconverting Nanoparticle Compositions

The present disclosure provides compositions with enhanced efficiency of upconverting near infra-red radiation to provide red emission.

The nanoparticle compositions as provided herein comprise an alkali metal rare earth fluoride composition according to the formula $M^1M^2F_4$ comprising lanthanide ions, wherein $M^1$ is the alkali metal, $M^2$ is the rare earth, and wherein the composition comprises ytterbium in an amount from about 70 mol % to about 99 mol % of the rare earth present in the composition; erbium in an amount from about 0.1 mol % to about 10 mol % of the rare earth present in the composition; and yttrium in an amount from about 0 mol % to about 30 mol % of the rare earth present in the composition.

In some embodiments, the alkali metal is sodium. In some embodiments, the alkali metal is lithium. In some embodiments, the alkali metal is potassium. Sodium is preferred.

While not being limited by any theory, it is understood that the compositions as provided herein can correspond in structure to sodium yttrium fluoride in which a portion of the yttrium atoms have been replaced by lanthanide atoms, and accordingly the composition can be referred to as comprising a "lanthanide doped" sodium yttrium fluoride composition. Due to the phenomenon of the lanthanide contraction, the lanthanide atoms are of comparable size to the yttrium atoms and can replace yttrium atoms in the sodium yttrium fluoride lattice. Accordingly, the upconverting nanoparticle compositions as described herein can have a formula $NaY_{0-0.3}Yb_{0.7-0.99}Er_{0.001-0.1}F_4$. Alternatively, the formula can be expressed as $NaYF_4$: Yb(70-99%)Er(0.01-10%), wherein the percentages in parentheses indicate the percentage of yttrium atoms replaced by ytterbium and erbium atoms respectively. The composition can have a cubic structure (α) or a hexagonal structure (β) corresponding to the structure of cubic (α) or hexagonal (β) $NaYF_4$. In some embodiments, the composition has a cubic structure (α) or α $NaYF_4$. In some embodiments, the composition has a hexagonal structure (β) or β $NaYF_4$.

In the compositions provided herein, ytterbium can be present in an amount from about 70 mol % to about 99 mol % of the rare earth present in the composition. For example, the composition can comprise ytterbium in an amount of about 70, 75, 80, 85, 90, 95, 96, 97, 98, or 99 mol % of the rare earth present in the composition or within a range between any of these values, for example from about 70 mol % to about 98 mol %, from about 70 mol % to about 95 mol %, from about 70 mol % to about 90 mol %, from about 70 mol % to about 85 mol %, from about 75 mol % to about 98 mol %, from about 75 mol % to about 95 mol %, from about 75 mol % to about 90 mol %, from about 75 mol % to about 85 mol %, from about 80 mol % to about 98 mol %, from about 80 mol % to about 95 mol %, from about 80 mol % to about 90 mol %, from about 80 mol % to about 85 mol %, of the rare earth present in the composition.

In the compositions provided herein, erbium can be present in an amount from about 0.1 mol % to about 10 mol % of the rare earth present in the composition. For example, the composition can comprise erbium in an amount of about 0.1, 0.2, 0.3, 0.4, 0.5, 1, 1.5, 2, 2.5, 3, 4, 5, 6, 7, 8, 9, or 10 mol % of the rare earth present in the composition or within a range between any of these values, for example from about 0.1 mol % to about 10 mol %, from about 0.1 mol % to about 5 mol %, from about 0.1 mol % to about 3 mol %, from about 0.1 mol % to about 2 mol %, from about 0.5 mol % to about 10 mol %, from about 0.5 mol % to about 5 mol %, from about 0.5 mol % to about 3 mol %, from about 0.5 mol % to about 2 mol %, about 1 mol % to about 10 mol %, from about 1 mol % to about 5 mol %, from about 1 mol % to about 3 mol %, from about 1 mol % to about 2 mol %, from about 2 mol % to about 10 mol %, from about 2 mol % to about 5 mol %, from about 1.5 mol % to about 3 mol %, or from about 1.5 mol % to about 2.5 mol % of the rare earth present in the composition.

In the compositions provided herein, yttrium can be present in an amount from about 0 mol % to about 30 mol % of the rare earth present in the composition. For example, the composition can comprise yttrium in an amount of about 0, 0.1, 0.2, 0.3, 0.4, 0.5, 1, 1.5, 2, 2.5, 5, 10, 15, 20, 25 or 30 mol % of the rare earth present in the composition, or within a range between any of these values, for example from about 0 mol % to about 30 mol %, 0 mol % to about 25 mol %, 0 mol % to about 20 mol %, 0 mol % to about 15 mol %, 0 mol % to about 10 mol %, 0 mol % to about 5 mol %, 0 mol % to about 2 mol %, 0 mol % to about 1 mol %, 0 mol % to about 30 mol %, 0 mol % to about 30 mol %, 0.1 mol % to about 30 mol %, 0.1 mol % to about 25 mol %, 0.1 mol % to about 20 mol %, 0.1 mol % to about 15 mol %, 0.1 mol % to about 10 mol %, 0.1 mol % to about 5 mol %, 0.1 mol % to about 2 mol %, 0.1 mol % to about 1 mol %, 1 mol % to about 30 mol %, 1 mol % to about 25 mol %, 1 mol % to about 20 mol %, 1 mol % to about 15 mol %, 1 mol % to about 10 mol %, 1 mol % to about 5 mol %, 1 mol % to about 2 mol %, 5 mol % to about 30 mol %, 5 mol % to about 25 mol %, 5 mol % to about 20 mol %, 5 mol % to about 15 mol %, 5 mol % to about 10 mol %, 10 mol % to about 30 mol %, 10 mol % to about 25 mol %, 10 mol % to about 20 mol % of the rare earth present in the composition.

In some compositions, the compositions comprise ytterbium, erbium and yttrium, as the rare earth metals present in the compositions. In some compositions, the compositions consist essentially of ytterbium, erbium and yttrium as the rare earth metals present in the compositions. In some compositions, the compositions consist of ytterbium, erbium and yttrium as the rare earth metals present in the compositions.

In some compositions, the compositions comprise ytterbium and erbium as the lanthanides present in the compositions. In some compositions, the compositions consist essentially of ytterbium and erbium as the lanthanide metals present in the compositions. In some compositions, the compositions consist of ytterbium and erbium as the lanthanide metals present in the compositions.

In certain preferred embodiments, upconverting composition described herein is in the form of nanoparticles. The nanoparticles may have any suitable dimensions, for example, with a dimension. Typically the dimension of the nanoparticle ranges from about 2 nm to about 150 nm (e.g., from about 2 nm to about 100 nm, from about 3 nm to about 50 nm, from about 5 nm to about 30 nm).

While not being limited by any theory, it is believed that the enhanced upconversion efficiency is achieved by providing an increased ratio of ytterbium compared to yttrium and erbium in the sodium ytterbium fluoride core structure. For example, an $NaYF_4$:Yb,Er composition containing a core ytterbium ratio of 98% ($NaYF_4$:Yb(98%),Er(2%)) provided 15 times greater red emission compared to a $\beta$-$NaYF_4$:Yb,Er composition containing a core ytterbium ratio of 20% ($NaYF_4$:Yb(20%),Er(2%)).

Figure 1B:
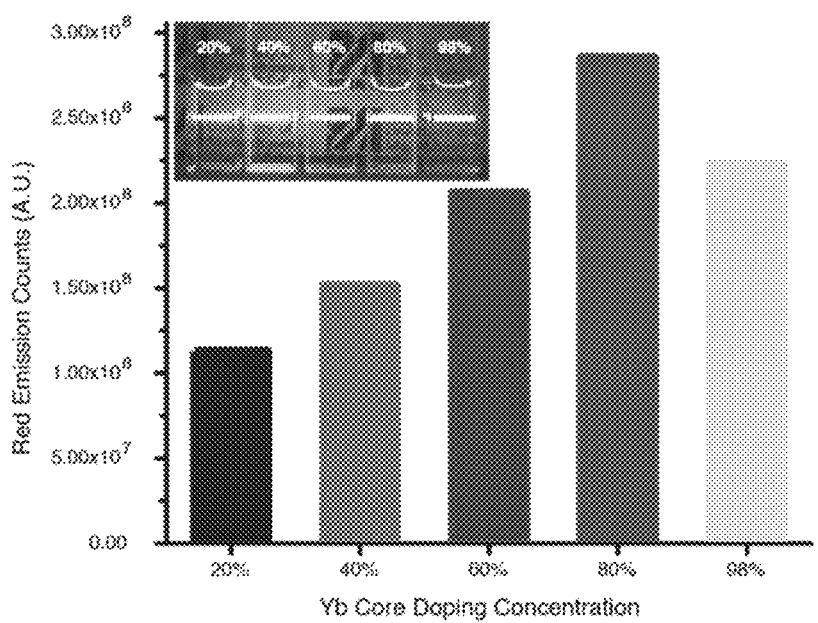
FIG. 1B: Integrated counts of red-emission and photographs (inset) of α-NaYF$_4$:Yb,Er@CaF$_2$ UCNPs with different Yb-levels from 20 to 98%.

In developing the compositions of the present invention, a series of calcium fluoride coated $\alpha$-$NaYF_4$:Yb,Er(2%)@$CaF_2$ UCNPs with escalated ytterbium ratios (i.e., 20%, 40%, 60%, 80%, 98%) by a synthesis procedure similar to that described by Shen et al., *Small*, 2013, 9, 3213-3217 and the supporting information thereto. Emission spectra under CW 980 nm 1 W/cm$^2$ showed that the red emission of these UCNPs increased as the ytterbium core doping ratio increased from 20% to 80% as shown in FIG. 1A. Integrated counts between 600 and 700 nm and corresponding photographs revealed that there was a 250% percent increase in red-emissions from $\alpha$-$NaYF_4$:Yb(20%),Er(2%)@$CaF_2$ to $\alpha$-$NaYF_4$:Yb(80%),Er(2%)@$CaF_2$ as shown in FIG. 1B. Furthermore, the red emission of $\alpha$-$NaYF_4$:Yb(80%),Er(2%)@$CaF_2$ is 15 times as strong as that of $\beta$-$NaYF_4$:Yb(20%),Er(2%)@ $\beta$-$NaYF_4$, which was previously considered an optimal red-emitting upconverting nanoparticle structure, as demonstrated by FIG. 2.

In addition, the extinction coefficient of upconverting nanoparticles could also be increased 4 times by elevating the concentration of ytterbium from 20% to 80%. In this case, the composition containing 98% ytterbium ($\alpha$-$NaYbF_4$:Yb(98%),Er(2%)@$CaF_2$), had slightly less red-emission than a composition containing 80% ytterbium ($\alpha$-$NaYbF_4$:Yb(80%),Er(2%)@$CaF_2$).

Figure 3:
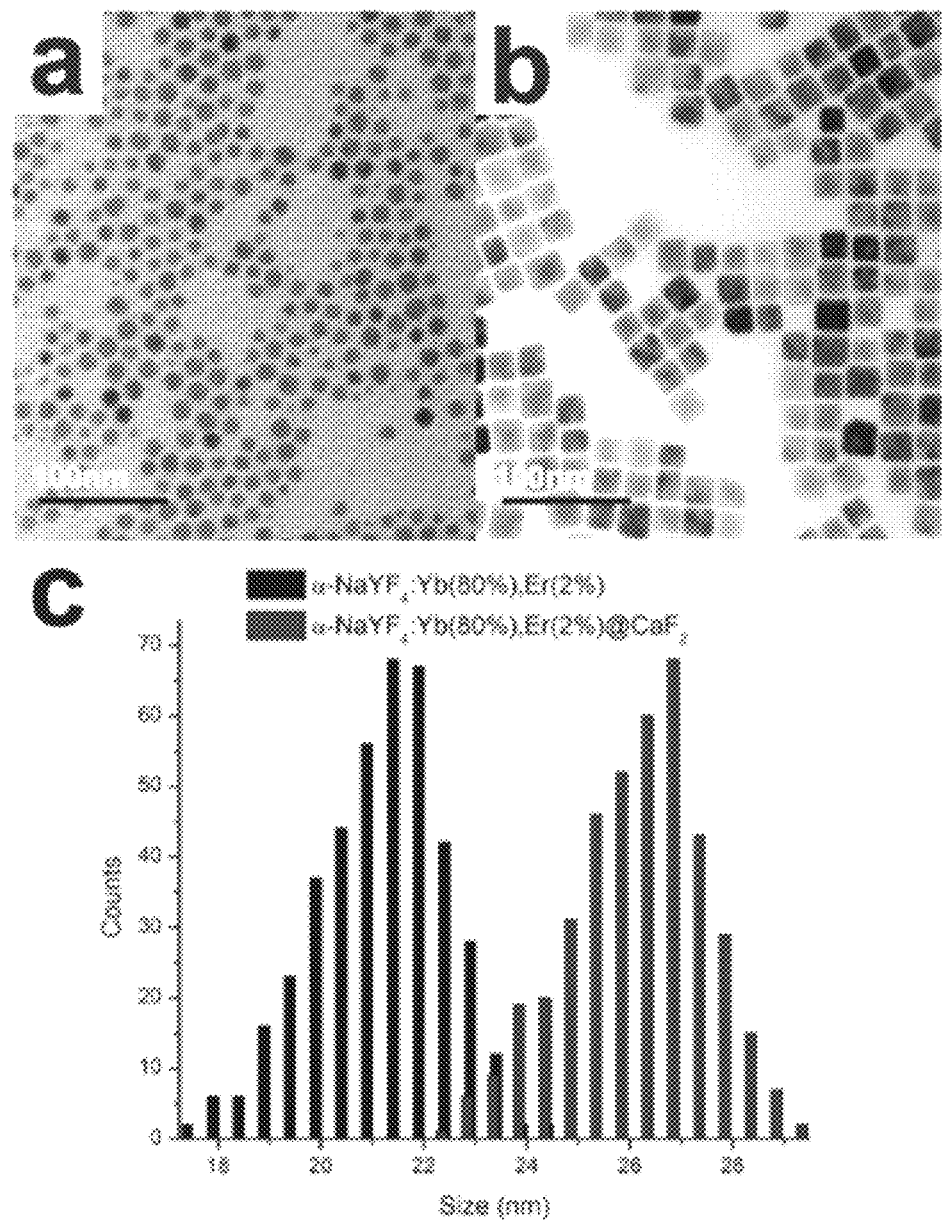
FIG. 3: TEM images of (a) uncoated upconverting nanoparticles containing an 80% molar ratio of ytterbium and (b) calcium fluoride coated upconverting nanoparticles containing an 80% molar ratio of ytterbium; and (c) a plot of the size distributions of the uncoated and coated upconverting nanoparticles (left peak—uncoated; right peak CaF$_2$ coated).

Under TEM imaging, the 80% ytterbium nanoparticles showed a distinct size distribution as shown in FIG. 3, indicating and were consistent with the particles having a core/shell structure.

Figure 4:
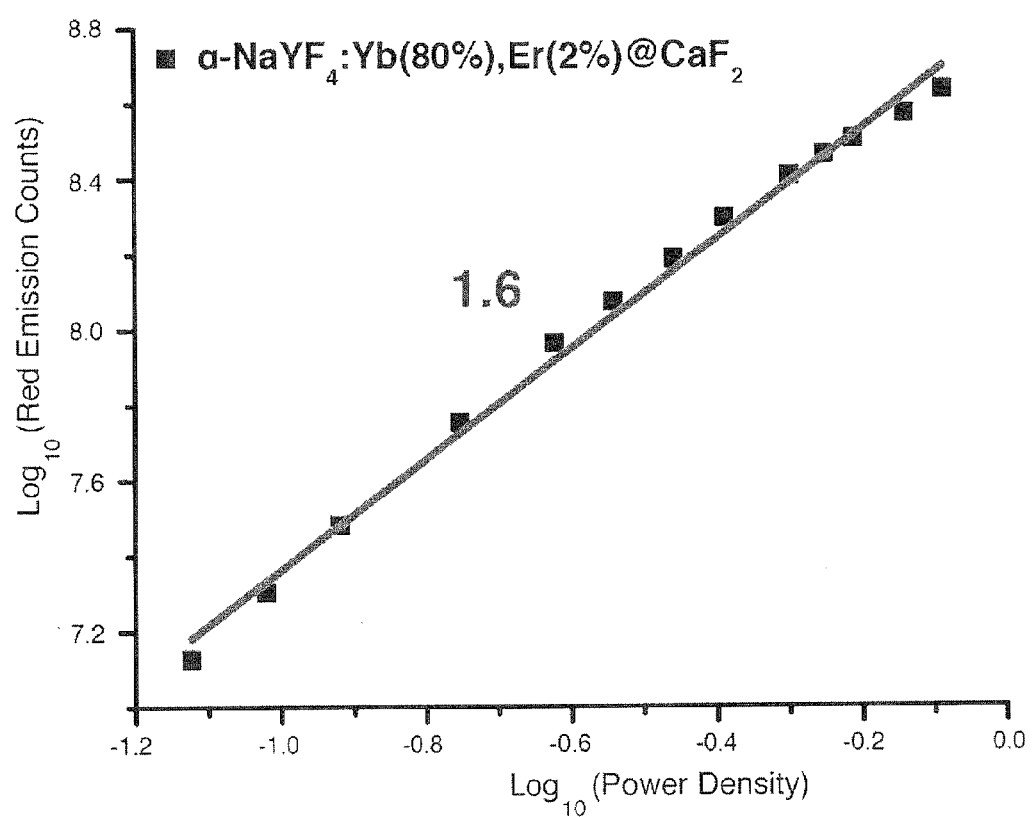
FIG. 4: Plot of the power dependence of red emission fluorescence from calcium fluoride coated upconverting nanoparticles containing an 80% molar ratio of ytterbium with the slope of 1.6 indicating that the fluorescence results from a two-photon process.

The power-dependent curve of red-emission from $\alpha$-$NaYF_4$:Yb(80%),Er(2%)@$CaF_2$ shown in FIG. 4 indicates that the luminescence is a two-photon upconverting process.

Coating Compositions

The upconverting nanoparticles provided in the present disclosure can be coated with a shell material that can, for example, serve to reduce the leakage of potentially toxic heavy metal ions such as lanthanides from the upconverting nanoparticles. This can increase the suitability of the upconverting nanoparticles for in vivo applications. A shell can also serve to reduce quenching of fluorescence from the upconverting nanoparticle core as a result of surface effects. The nanoparticles can therefore have a core/shell configuration, preferably an epitaxial configuration.

The coating material used for coating the upconverting nanoparticles provided in the present disclosure is preferably optically transparent, particularly in the red and infra-red regions of the spectrum, and preferably has low solubility or is substantially insoluble in water so that the coating can be stable when the upconverting nanoparticle is subjected to aqueous medium.

In some embodiments, the shell material comprises, consists essentially of or consists of calcium fluoride ($CaF_2$). While not being limited by any theory, it is understood that calcium fluoride is suitable as a shell material due to its optical transparency, stability, and small lattice, which mismatches with that of $NaYF_4$. Since calcium fluoride is a component of ossified tissues, calcium fluoride shells can inhibit or prevent ion leakage and have good biocompatibility.

Other materials that may be useful as a shell of the upconverting nanoparticles described herein include includes $NaYF_4$ ($\alpha$ or $\beta$), $CaF_2$, $LiYF_4$, $NaGdF_4$, $NaScF_4$, $NaYbF_4$, $NaLaF_4$, $LaF_3$, $GdF_3$, $GdOF$, $La_2O_3$, $Lu_2O_3$, $Y_2O_3$, $Y_2O_2S$, $YbF_3$, $YF_3$, $KYF_4$, $KGdF_4$, $BaYF_5$, $BaGdF_5$, $NaLuF_4$, $KLuF_4$, and $BaLuF_5$.

In certain embodiments, the core has a dimension from about 1 nm to about 100 nm (e.g., about 2 nm, about 5 nm, about 10 nm, about 20 nm, about 30 nm, about 40 nm, about 50 nm, about 60 nm, about 70 nm, about 80 nm, about 90 nm) and the shell has a thickness from about 1 nm to about 50 nm (e.g., about 2 nm, about 5 nm, about 10 nm, about 20 nm, about 30 nm, about 40 nm).

Synthesis

The upconverting nanoparticles described herein may be prepared according to methods analogous to those known in the art for preparing upconverting nanoparticles. The ratio of rare earths present is controlled to provide the desired ratio of rare earths present in the nanoparticle. For example, to provide a nanoparticle with a core composition in comprising ytterbium in an amount from about 70 mol % to about 99 mol % of the rare earth present in the composition; erbium in an amount from about 0.1 mol % to about 10 mol % of the rare earth present in the composition; and yttrium in an amount from about 0 mol % to about 30 mol % of the rare earth present in the composition, ytterbium, erbium and yttrium would be used in corresponding ratios in the synthesis of the nanoparticle. General synthesis methods are discussed in Chen, et al., Upconversion Nanoparticles: Design, Nanochemistry, and Applications in Theranostics, *Chem. Rev.*, 2014, 114, 5161.

In some embodiments, a method is provided of preparing an upconverting nanoparticle, wherein the method comprises reacting in a reaction mixture rare earth trifluoroacetates and an alkali metal (e.g., sodium) trifluoroacetate under conditions sufficient to form a sodium rare earth tetrafluoride, wherein the rare earth trifluoroacetates are selected from the group consisting of: ytterbium trifluoroacetate in an amount from about 70 mol % to about 99 mol % of the rare earth trifluoroacetates present in the reaction mixture; erbium trifluoroacetate in an amount from about 0.1 mol % to about 10 mol % of the rare earth trifluoroacetates present in the reaction mixture; and yttrium trifluoroacetate in an amount from about 0 mol % to about 30 mol % of the rare earth trifluoroacetates present in the reaction mixture. In some embodiments, the rare earth trifluoroacetates present in the mixture comprise, consist essentially of, or consist of ytterbium trifluoroacetate, erbium trifluoroacetate and (optionally) yttrium trifluoroacetates, wherein the rare earth trifluoroacetates are present in a ratio to provide the ratio desired in the nanoparticle. In some embodiments, the rare earth trifluoroacetates comprise, consist essentially of or consist of ytterbium trifluoroacetate in an amount of about 80 mol % of the rare earth trifluoroacetates present in the reaction mixture; erbium trifluoroacetate in an amount of about 2 mol % of the rare earth trifluoroacetates present in the reaction mixture; and yttrium trifluoroacetate in an amount of about 18 mol % of the rare earth trifluoroacetates present in the reaction mixture. Also provided are nanoparticles prepared according to such methods.

In some embodiments, the synthesis methods include reacting the rare earth trifluoroacetates and alkali metal trifluoroacetate at high temperature, for example about 300° C., in a high boiling solvent such as octadecene, and in the presence of a suitable capping agent to prevent nanoparticle aggregation such as oleic acid, oleylamine or trioctylphosphine oxide, or the like. By tailoring the experimental variables, such as the nature of the solvents, concentration of metal precursors, reaction temperature, and time, high-quality UCNPs with a narrow size distribution, good crystallinity, and optical properties can be obtained from the thermolysis process and the composition and structure of the nanoparticles can be controlled.

In the methods provided herein, ytterbium trifluoroacetate can be present in an amount from about 70 mol % to about 99 mol % of the rare earth trifluoroacetate present in the reaction mixture. For example, the reaction mixture can comprise ytterbium trifluoroacetate in an amount of about 70, 75, 80, 85, 90, 95, 96, 97, 98, or 99 mol % of the rare earth trifluoroacetate present in the reaction mixture or within a range between any of these values, for example from about 70 mol % to about 98 mol %, from about 70 mol % to about 95 mol %, from about 70 mol % to about 90 mol %, from about 70 mol % to about 85 mol %, from about 75 mol % to about 98 mol %, from about 75 mol % to about 95 mol %, from about 75 mol % to about 90 mol %, from about 75 mol % to about 85 mol %, from about 80 mol % to about 98 mol %, from about 80 mol % to about 95 mol %, from about 80 mol % to about 90 mol %, from about 80 mol % to about 85 mol %, of the rare earth trifluoroacetate present in the reaction mixture.

In the methods provided herein, erbium trifluoroacetate can be present in an amount from about 0.1 mol % to about 10 mol % of the rare earth present in the reaction mixture. For example, the reaction mixture can comprise erbium trifluoroacetate in an amount of about 0.1, 0.2, 0.3, 0.4, 0.5, 1, 1.5, 2, 2.5, 3, 4, 5, 6, 7, 8, 9, or 10 mol % of the rare earth trifluoroacetate present in the reaction mixture or within a range between any of these values, for example from about 0.1 mol % to about 10 mol %, from about 0.1 mol % to about 5 mol %, from about 0.1 mol % to about 3 mol %, from about 0.1 mol % to about 2 mol %, from about 0.5 mol % to about 10 mol %, from about 0.5 mol % to about 5 mol %, from about 0.5 mol % to about 3 mol %, from about 0.5 mol % to about 2 mol %, about 1 mol % to about 10 mol %, from about 1 mol % to about 5 mol %, from about 1 mol % to about 3 mol %, from about 1 mol % to about 2 mol %, from about 2 mol % to about 10 mol %, from about 2 mol % to about 5 mol %, from about 1.5 mol % to about 3 mol %, or from about 1.5 mol % to about 2.5 mol % of the rare earth trifluoroacetate present trifluoroacetate present in the reaction mixture.

In the methods provided herein, yttrium trifluoroacetate can be present in an amount from about 0 mol % to about 30 mol % of the rare earth trifluoroacetate present in the reaction mixture. For example, the reaction mixture can comprise yttrium trifluoroacetate in an amount of about 0, 0.1, 0.2, 0.3, 0.4, 0.5, 1, 1.5, 2, 2.5, 5, 10, 15, 20, 25 or 30 mol % of the rare earth trifluoroacetate present in the reaction mixture, or within a range between any of these values, for example from about 0 mol % to about 30 mol %, 0 mol % to about 25 mol %, 0 mol % to about 20 mol %, 0 mol % to about 15 mol %, 0 mol % to about 10 mol %, 0 mol % to about 5 mol %, 0 mol % to about 2 mol %, 0 mol % to about 1 mol %, 0 mol % to about 30 mol %, 0 mol % to about 30 mol %, 0.1 mol % to about 30 mol %, 0.1 mol % to about 25 mol %, 0.1 mol % to about 20 mol %, 0.1 mol % to about 15 mol %, 0.1 mol % to about 10 mol %, 0.1 mol % to about 5 mol %, 0.1 mol % to about 2 mol %, 0.1 mol % to about 1 mol %, 1 mol % to about 30 mol %, 1 mol % to about 25 mol %, 1 mol % to about 20 mol %, 1 mol % to about 15 mol %, 1 mol % to about 10 mol %, 1 mol % to about 5 mol %, 1 mol % to about 2 mol %, 5 mol % to about 30 mol %, 5 mol % to about 25 mol %, 5 mol % to about 20 mol %, 5 mol % to about 15 mol %, 5 mol % to about 10 mol %, 10 mol % to about 30 mol %, 10 mol % to about 25 mol %, 10 mol % to about 20 mol % of the rare earth trifluoroacetate present in the reaction mixture.

Photodynamic Therapy Agents

The upconverting nanoparticles described herein may be used in conjunction with a photodynamic therapy agent for the treatment of, e.g., cancer and other diseases.

A wide array of photosensitizers for suitable for photodynamic therapy can be used in conjunction with the nanoparticles provided in this disclosure. Suitable classes of photosensitizer that can be used include porphyrins, chlorophylls and dyes. Examples of suitable photosensitizers include aminolevulinic acid, silicon phthalocyanine Pc 4, m-tetrahydroxyphenylchlorin, and mono-L-aspartyl chlorin e6.

Examples of photosensitizers that are commercially available or being developed for clinical use, and which are useful for use with the nanoparticles disclosed herein include such as hexyl aminolevulinate (Allumera™, Cevira™, Hexvix™), porfimer sodium (Photofrin™), verteporfin (Visudyne™), δ-aminolevulinic acid or 5-aminolevulinic acid (Levulan™), temoporfin (Foscan™), methyl aminolevulinate (Metvix™), hexaminolevulinate hydrochloride (Cysview™), talaporfin (Laserphyrin™) motexafin lutetium (Antrin™), 2-(1-hexyloxyethyl)-2-devinyl pyropheophorbide-a (Photochlor™), Photosens™ (mixture of sulfonated aluminium phthalocyanines with various degrees of sulfonation), rostaporfin (Photrex™, SnET2, Purlytin™), BF-200 ALA (nanoemulsion BF-200 with 5-aminolevulinic acid), tetraphenyl chlorin disulfonate (TPCS2a, Amphinex™) and azadipyrromethene.

In one embodiment, the photosensitizing agent is 5-aminolevulinic acid. 5-Aminolevulinic acid is a compound in the porphyrin synthesis pathway, the pathway that leads to heme in mammals and chlorophyll in plants. It elicits synthesis and accumulation of fluorescent porphyrins (protoporphyrin IX) in epithelia and neoplastic tissues. 5-Aminolevulinic acid therefore acts precursor of a photosensitizer.

In some embodiments, the photodynamic therapy agent can be administered to a patient separately from the nanoparticles provided in the present disclosure, for example systemically administered, or administered locally or topically at the site to be treated.

In some embodiments, the photodynamic therapy agent can be attached to the nanoparticle through a suitable point for covalent attachment. In some embodiments, the nanoparticle of the disclosure can be coated with a suitable functionalized polymer where the functional groups of the polymer can serve as a point of attachment for the photodynamic therapy agent. Examples of suitable polymers include polyacrylate polymers, poly(lactide), poly(glycolide), poly(lactic co-glycolic acid), poly(arylates), poly(anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly(malic acid), poly(methyl vinyl ether), poly(ethylene imine), poly(acrylic acid), poly(maleic anhydride), biodegradable polyurethanes and polysaccharides, alginate, starches, dextrans, celluloses, chitin, chitosan, hyaluronic acid and its derivatives. Naturally-occurring polymers, such as polysaccharides and proteins, may be used. Exemplary proteins including collagen, albumin, and gelatin. Exemplary polysaccharides include starches, dextrans, and celluloses, including derivatives thereof such as ether and ester derivatives. In other embodiments, the polymer includes polyhydroxy acids such as polylactic acid (PLA), polyglycolic acid (PGA), their copolymers poly(lactic-co-glycolic acid) (PLGA), and mixtures of any of these. In certain embodiments, the particles include poly(lactic-co-glycolic acid) (PLGA). Non-biodegradable polymers may also be used. Exemplary non-biodegradable, but biocompatible polymers include polystyrene, polyesters, non-biodegradable polyurethanes, polyureas, poly(vinyl alcohol), polyamides, poly(tetrafluoroethylene), poly(ethylene vinyl acetate), polypropylene, polyacrylate, non-biodegradable polycyanoacrylates, non-biodegradable polyurethanes, polymethacrylate, poly(methyl methacrylate), polyethylene, polypyrrole, polyanilines, polythiophene, and poly(ethylene oxide). Any of the polymers may be functionalized with a poly(alkylene glycol), for example, poly(ethylene glycol) (PEG) or poly(propyleneglycol) (PPG), or any other hydrophilic polymer system. Some of the polymers may have a particular terminal functional group, such as a carboxylic acid group, that can be used to attach the photodynamic therapy agent.

The photodynamic therapy agent can be attached to the polymer via a linker. In its simplest form, a linker can be a covalent chemical bond. In other embodiments, the linker can be a chemical group. Since the function of the linking group is merely to provide a physical connection, a wide variety of chemical groups can serve as linking groups. A linker is typically a divalent organic linking group where one valency represents the point of attachment the polymer and one valency represents the attachment to the photodynamic therapy agent. The only requirement for the linker is to provide a stable physical linkage that is compatible with maintaining the function of the nanoparticle. Examples of suitable linking groups include, e.g.: O, S, S(O), S(O)$_2$, C(O), NH, N(C$_{1-6}$)alkyl, NHC(O), C(O)NH, O(CO), C(O)O, O(CO)NH, NHC(O)O, O(CO)O, NHC(O)NH, O(C$_{1-6}$)alkylene, S(C$_{1-6}$)alkylene, S(O)(C$_{1-6}$)alkylene, S(O)$_2$(C$_{1-6}$)alkylene, C(O)(C$_{1-6}$)alkylene, NH((C$_{1-6}$)alkylene)C(O), C(O)((C$_{1-6}$)alkylene)C(O), C(O)((C$_{1-6}$)alkylene)NH, —N=C<, >C=NH—, —C(O)NH—N=C<, >C=NH—NHC(O), unsubstituted(C$_{1-6}$)alkylene, unsubstituted(C$_{1-10}$) heteroalkylene, or (C$_{1-10}$)alkylene, unsubstituted (C$_{1-10}$)heteroalkylene, substituted with one or more (e.g., 1, 2, 3, 4 or 5 substituents) independently selected from the group consisting of (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, OC(=O)Ar, —C(=O)OR, —C(=O)NR$_2$, C(=NR)NR$_2$, —OR, Ar, OAr, ((C$_{1-6}$)alkylene)Ar, O((C$_{1-6}$)alkylene)Ar, OC(=O)(C$_{1-6}$)alkyl, OC(=O)O(C$_{1-6}$)alkyl, —OC(=O)NR$_2$, —NR$_2$, NRAr, NR((C$_{1-6}$)alkylene)Ar, NRC(=O)R, NRC(=O)Ar, —NRC(=O)O(C$_{1-6}$)alkyl, NRC(=O)NR$_2$, —NRSO$_2$R, SR, —S(O)R, —SO$_2$R, —OSO$_2$(C$_{1-6}$)alkyl, —SO$_2$NR$_2$, (C$_1$-C$_8$)perfluoroalkyl, (C$_{2-6}$)alkylene-OR, O(C$_{2-6}$)alkylene-N((C$_{1-6}$)alkyl)$_2$, —P(=O)(OR)$_2$, OP(=O)(OR)$_2$, wherein each R group is hydrogen or (C$_{1-6}$ alkyl), e.g., methyl and wherein each Ar is independently unsubstituted aryl or heteroaryl or aryl or heteroaryl substituted with one or more of (C$_{1-6}$)alkyl, (C$_{2-6}$)alkenyl, (C$_{2-6}$)alkynyl, halogen, (C$_{1-6}$)haloalkyl, —CN, NO$_2$, C(=O)R, —C(=O)OR, —C(=O)NR$_2$, C(=NR)NR$_2$, —OR, OC(=O)(C$_{1-6}$)alkyl, OC(=O)O(C$_{1-6}$)alkyl, —OC(=O) NR$_2$, NR$_2$, —NRC(=O)R, NRC(=O)O(C$_{1-6}$)alkyl, NRC(=O)NR$_2$, —NRSO$_2$R, —SR, S(O)R, —SO$_2$R, —OSO$_2$(C$_{1-6}$)alkyl, —SO$_2$NR$_2$, (C$_1$-C$_8$)perfluoroalkyl, (C$_{2-6}$)alkylene-OR, O(C$_{2-6}$)alkylene-N((C$_{1-6}$)alkyl)$_2$, P(=O)(OR)$_2$, OP(=O)(OR)$_2$ wherein each R group is hydrogen or (C$_{1-6}$alkyl). In addition, (C$_{1-10}$)alkylene and (C$_{1-10}$)heteroalkylene can be substituted by one or more oxo groups (C=O) and the nitrogen and sulfur atoms of a heteroalkylene group can optionally be oxidized (e.g., to form S(O), S(O)$_2$, or N-oxide). Suitable heteroalkylene groups can include one or more 1,2-dioxyethylene units (OCH$_2$CH$_2$)$_n$O, where n is an integer, e.g., 1, 2, 3, 4 or 5). The (C$_{1-10}$) alkylene and (C$_{1-10}$)heteroalkylene also include (C$_{1-6}$)alkylene and (C$_{1-6}$)heteroalkylene and (C$_{1-3}$)alkylene and (C$_{1-3}$)heteroalkylene.

In some embodiments, the linking group may be cleavable under conditions under which release of the photodynamic therapy agent is desirable. In some embodiments, the linking group may be formed by reaction of functional groups of the polymer, or functional groups of the linking group, with functional groups of the photodynamic therapy agent (or by reaction of functional groups of the photodynamic therapy agent, or functional groups of the linking group, with functional groups of the polymer) so that the moiety attached to the polymer is a precursor of the photodynamic therapy agent, and the photodynamic therapy agent is formed upon release from the polymer.

For example, the linking group may be cleavable metabolically (e.g., by enzymes) or under particular chemical conditions found in a particular part of the body or particular cell (e.g., low pH conditions). Examples of cleavable linking groups include, e.g.: NHC(O), C(O)NH, O(CO), C(O)O, O(CO)NH, NHC(O)O, O(CO)O, NHC(O)NH, O($C_{1-6}$)alkylene (particularly alkylene groups with a single linking carbon atom), —N=C<, >C=NH—, —C(O)NH—N=C<, >C=NH—NHC(O)—.

In an example, one kind of linking group is a hydrazone group of formula —C(O)NH—N=C< or >C=NH—NHC(O)— which can be cleaved to release the photodynamic therapy agent under acidic conditions. A hydrazone group can be formed, e.g., by reaction of a C=O group or hydrazone group attached to or forming part of the polymer with a hydrazone group or C=O group attached to or forming part of the photodynamic therapy agent. The hydrazone and C=O groups can be re-formed by hydrolysis of the hydrazone group under suitable conditions.

Figure 5:
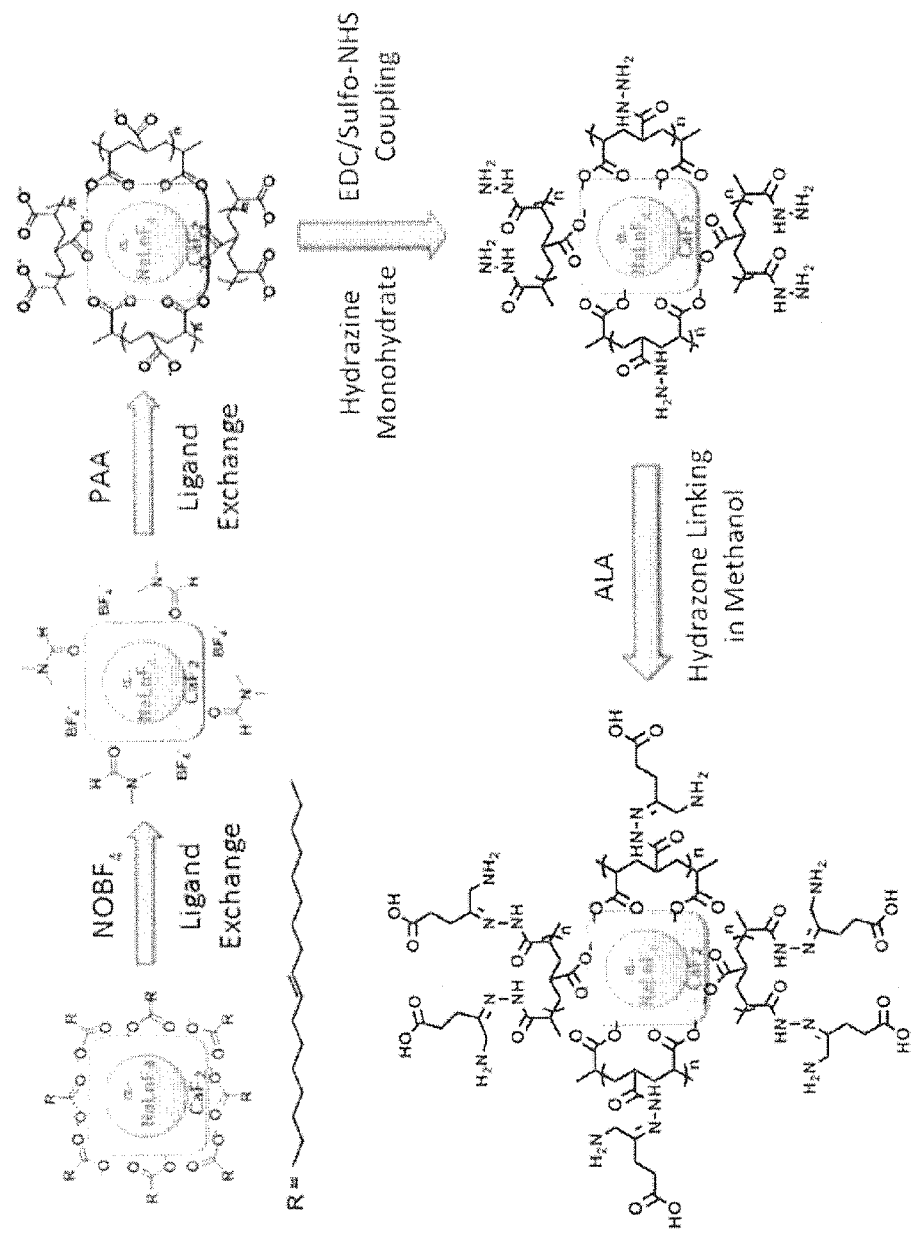
FIG. 5: Diagram illustrating the process of conjugating 5-aminolevulinic acid to upconverting nanoparticles UCNPs via a pH-responsive hydrazone linkage.

In an exemplary embodiment provided herein, the prodrug 5-aminolevulinic acid (5-ALA) to the described above by means of a covalent hydrazone linkage to avoid possible pre-leaking of the 5-ALA and thereby increase its bioavailability. α-NaYF$_4$:Yb(80%),Er(2%)@CaF$_2$ upconverting nanoparticles were functionalized for the aqueous phase and conjugated ALA with a pH-sensitive hydrazone linkage via the method represented in FIG. 5. While not being limited by any theory, it is understood that by providing a pH-sensitive linkage, the conjugated 5-ALA can be released from the nanoparticle after the nanoparticle enters a cell due to the low pH of the endosome. Following release, it is understood that the 5-ALA can then diffuse to the mitochondria and cause the overproduction of protoporphyrin IX (PpIX).

The 5-ALA-conjugated upconverting nanoparticles described herein were also characterized morphologically.

Figure 6:
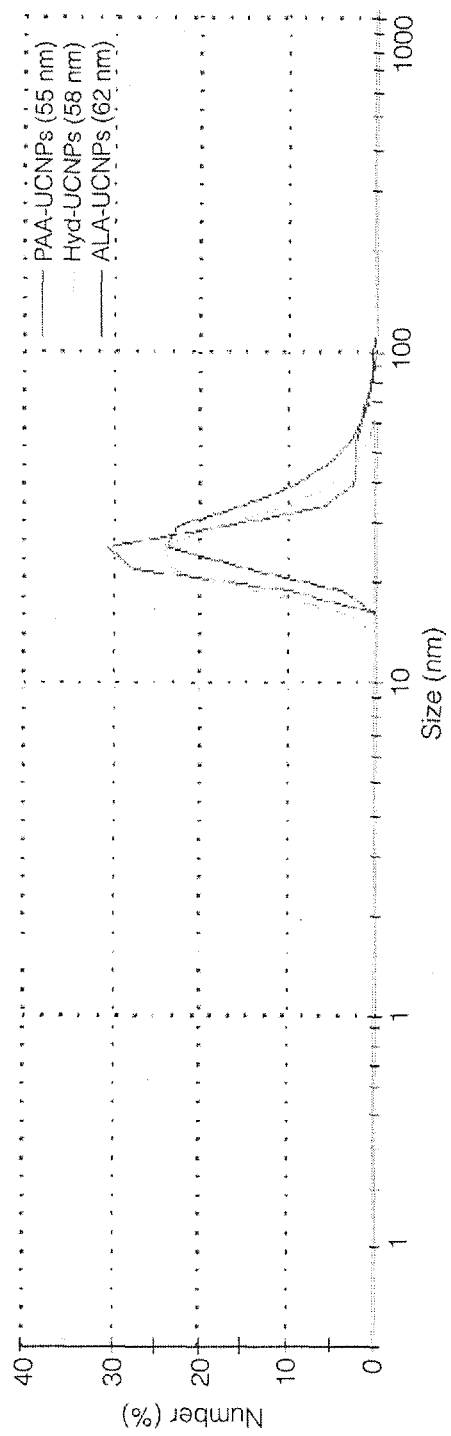
FIG. 6: Plot showing the size distributions of polyacrylic acid coated upconverting nanoparticles (PAA-UCNPs), hydrazide functionalized upconverting nanoparticles (Hyd-UCNPs), and 5-aminolevulinic acid functionalized upconverting nanoparticles (ALA-UCNPs) by number as determined by dynamic light scattering in PBS.

Dynamic light scattering was used to determine that the hydrodynamic size of the 5-ALA-conjugated nanoparticles was about 62 nm as shown in FIG. 6.

Figure 7:
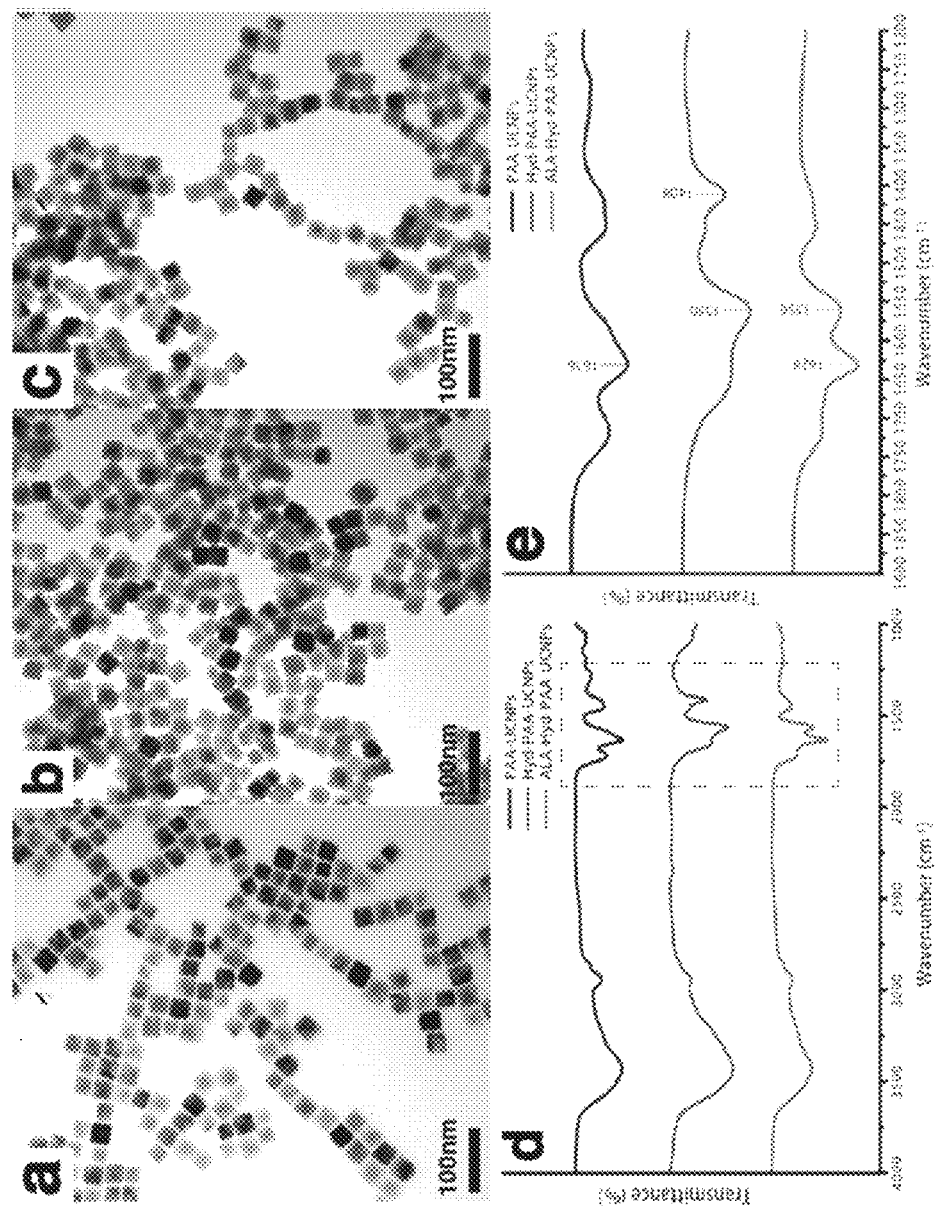
FIG. 7: TEM images of (a) polyacrylic acid coated upconverting nanoparticles (PAA-UCNPs), (b) hydrazide functionalized upconverting nanoparticles (Hyd-UCNPs), and (c) 5-aminolevulinic acid functionalized upconverting nanoparticles (ALA-UCNPs); and (d) full and (e) detailed FT-IR spectra of polyacrylic acid coated upconverting nanoparticles (PAA-UCNPs) compared with hydrazide functionalized upconverting nanoparticles (Hyd-UCNPs), and 5-aminolevulinic acid functionalized upconverting nanoparticles (ALA-UCNPs).

TEM images illustrate their monodispersity as shown in panels (a) to (c) of FIG. 7, which show, respectively, TEM images of (a) polyacrylic acid-coated upconverting nanoparticles (PAA-UCNPs), (b) hydrazide-functionalized upconverting nanoparticles (Hyd-UCNPs) and (c) 5-ALA-conjugated upconverting nanoparticles.

FT-IR spectral analysis confirmed that the conjugation of 5-ALA to the nanoparticles was via a hydrazone linkage as shown in panels (d) and (e) of FIG. 7, which show (d) full and (e) detailed spectra for polyacrylic acid-coated upconverting nanoparticles, (PAA-UCNPs), hydrazide-functionalized upconverting nanoparticles (Hyd-UCNPs) and 5-ALA-conjugated upconverting nanoparticles. On the spectrum for Poly(acrylic) acid-functionalized UCNPs (PAA-UCNPs), the peak at 1636 cm$^{-1}$ is attributed to the resonance of the carboxyl groups. However, this peak disappears after its amidation with hydrazine, as two new peaks at 1550 cm$^{-1}$ and 1408 cm$^{-1}$ (attributed to the N—H bending and stretching vibrations of NH$_3^+$ respectively). When the hydrazone linkage to 5-ALA is constructed, the peak at 1628 cm$^{-1}$ represents the —N=C— bond between the hydrazide-functionalized UCNPs (Hyd-UCNPs) and the 5-ALA and the retention of the peak at 1550 cm$^{-1}$ indicates the full acid-sensitive covalent linkage was successfully constructed between the 5-ALA and the UCNPs. High performance liquid chromatography was used to analyze the supernatants from the 5-ALA conjugation reactions and revealed a loading capacity of about 4.5 µmol/mg for 5-ALA onto the hydrazine-functionalized nanoparticles.

Therapeutic Applications of the Upconverting Nanoparticles

The terms "individual", "subject" or "patient," used interchangeably, refer to any animal, including mammals, preferably mice, rats, other rodents, rabbits, dogs, cats, swine, cattle, sheep, horses, or primates, and most preferably humans.

The phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician. When a combination of active agents is administered, the effective amount of the combination, or individual agents, may or may not include amounts of each agent that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

The upconverting nanoparticles provided by the present disclosure can be used for upconversion of infrared radiation for use in photodynamic therapy for example in the treatment of any condition that is treatable using photodynamic therapy to kill cells, e.g., any of the conditions discussed by Huang, A Review of Progress in Clinical Photodynamic Therapy, *Technol. Cancer Res. Treat,* 2005, 4(3), 283-293.

Examples of conditions that can be treated using photodynamic therapy employing upconverting nanoparticles as disclosed herein include skin diseases and conditions, skin cancer (e.g., basal cell carcinomas, squamous cell carcinoma, malignant melanomas and Kaposi's sarcoma, and secondary cancers originated from primary breast cancer, colon cancer, and endometrium cancer) as well as non-malignant skin conditions such as acne, psoriasis, warts and unwanted hair. Other conditions that can be treated include eye conditions such as age-related macular degeneration, choroidal neovascular disease, and choroidal haemangioma.

Conditions that can be treated using photodynamic therapy employing upconverting nanoparticles as disclosed herein further include infections, particularly localized infections, caused by bacteria, viruses, fungi and other pathogens, e.g., any of the conditions discussed by Kharkwal et al., *Lasers Surg. Med.*, 2011, 43(7), 705-707. Examples include viral lesions and infections (e.g., herpes simplex lesions, human papilloma virus infection, genital herpes, genital warts, papillomatosis, skin warts), bacterial and fungal lesions and infections (e.g., acne, erythrasma, rosacea, interdigital mycosis of the feet, tinea pedis, tinea cruris, ringworm, toenail onychomycosis, malassezia folliculitis, abscesses, including brain abscesses). Other infections that can be treated include dental infections, including dental caries and periodontal disease.

Conditions that can be treated using photodynamic therapy employing upconverting nanoparticles as disclosed herein also include cancers such as tumors, e.g., prostate cancer, gastroenterological cancer, colon cancer, esophageal cancer, endometrial cancer, ovarian cancer, uterine cancer, cervical cancer, renal cancer, hepatic cancer, pancreatic cancer, gastric cancer, breast cancer, lung cancer, cancers of the head or neck, thyroid cancer, glioblastoma, sarcoma, bladder cancer, testicular cancer and cholangiocarcinoma.

The methods of treatment can include administering to a subject in need of the treatment an effective amount of the nanoparticles as described herein, administering to the subject an effective amount of a photodynamic therapy agent (e.g., a photosensitizer or a precursor thereof), and subsequently administering to the subject an effective amount of infra-red radiation.

The nanoparticles as described herein can be locally administered or systemically administered provided that the administration, whether local or systemic, provides an effective concentration of the nanoparticles and the photodynamic therapy agent in the tissue to be treated. The nanoparticles and photodynamic therapy agent can be administered by the same or different routes and they can be administered simultaneously, sequentially, or in combination (e.g., for more than two agents). When the phototherapy agent is attached to the nanoparticles, the nanoparticles and photodynamic therapy agent are necessarily administered simultaneously and by the same route of administration.

The infra-red radiation is generally administered locally at the site to be treated.

Figure 8:
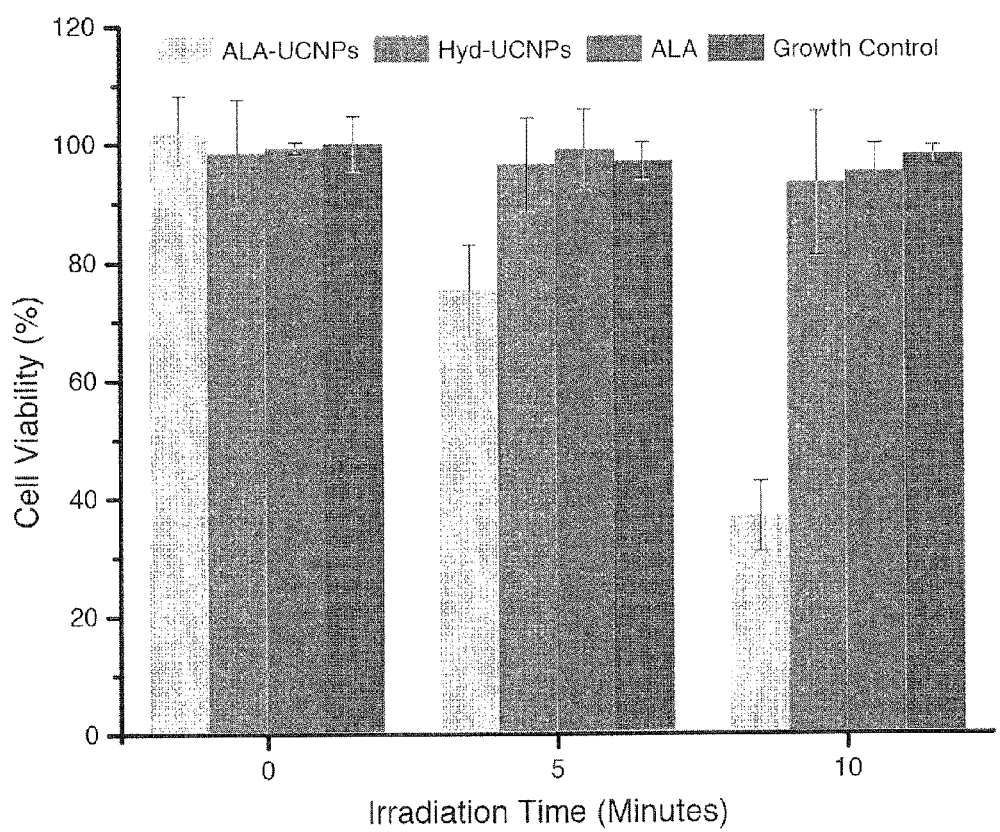
FIG. 8: Plots showing the viability of HeLa cells irradiated with CW 980 nm light at 1 W/cm$^2$ power density in the presence of 5-aminolevulinic acid functionalized upconverting nanoparticles and controls.

As a model to examine the efficacy of 5-aminolevulinic acid-conjugated upconverting particles as described herein, particles prepared as described herein (having an 80 mol % Yb content), a 3-(4,5-dimethylthiazol-2-yl)-2,5-diphenyltetrazolium bromide (MTT) proliferation assay was conducted to determine inhibition of cell proliferation using photodynamic therapy with the nanoparticles prepared as described herein. In the cell proliferation assay, HeLa cells were exposed to 5-aminolevulinic acid-conjugated upconverting particles and various controls (all 100 μg/mL) for 4 h and the cells were then irradiated by irradiation of continuous wave 980 nm light at 1 W/cm². The results of the assay are shown in FIG. 8, which depicts cell viability as a function of irradiation time. After 10 min. irradiation, the viability of cells exposed to 5-aminolevulinic acid-conjugated upconverting particles was only about 30%, corresponding to a killing rate of almost 70%, while cells exposed only to the presence of hydrazide-functionalized upconverting nanoparticles (no 5-aminolevulinic acid), 5-aminolevulinic acid in the absence of upconverting nanoparticles, or infra-red radiation alone showed minimal or no cytotoxicity.

Figure 9:
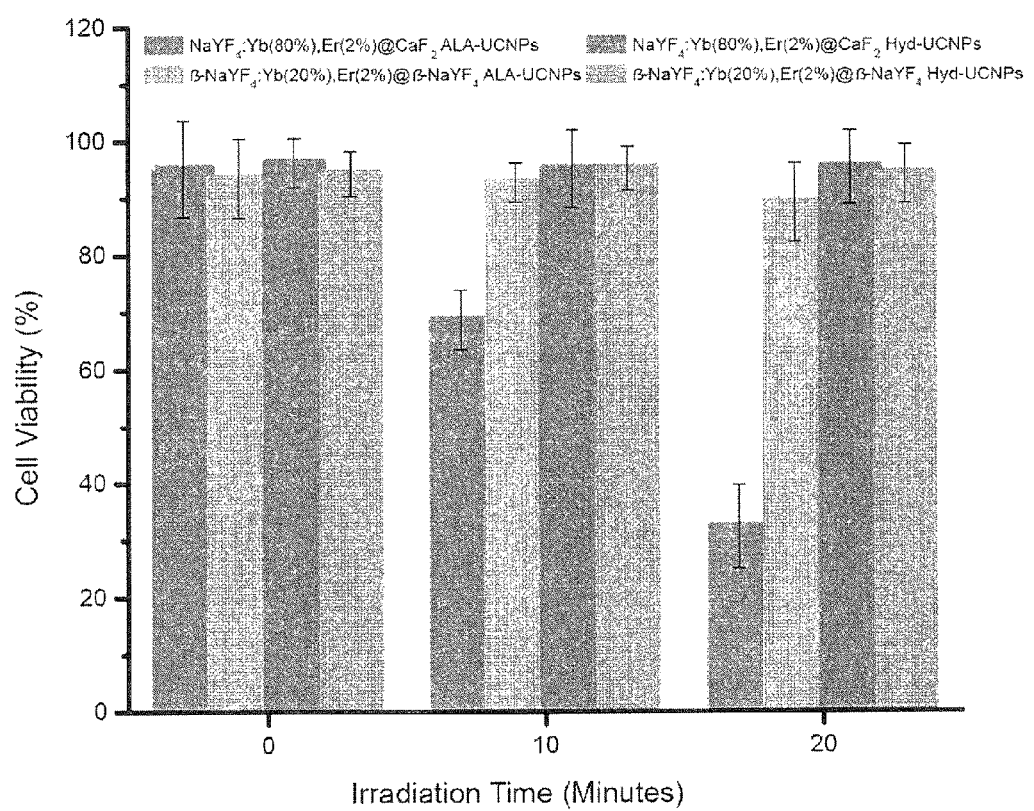
FIG. 9: Plots showing the viability of HeLa cells irradiated with CW 980 nm light at 0.35 W/cm$^2$ power density for calcium-fluoride coated upconverting nanoparticles containing 80% molar ratio ytterbium functionalized with 5-aminolevulinic acid and upconverting nanoparticles containing 20% molar ratio ytterbium functionalized with 5-aminolevulinic acid and controls.

The effectiveness of the upconverting nanoparticles described herein was also compared with upconverting nanoparticles containing lower levels of ytterbium Then, impact of the lanthanide-doped upconverting nanoparticles on 5-ALA-induced photodynamic therapy was evaluated. Upconverting nanoparticles as disclosed herein were compared with control upconverting nanoparticles containing 20% ytterbium and 2% erbium conjugated to 5-aminolevulinic acid (β-NaYF4:Yb(20%),Er(2%)@β-NaYF$_4$) having a similar 5-aminolevulinic acid loading capacity (i.e., ~4.5 μmol/mg). Cells exposed to these control nanoparticles were irradiated at a biocompatible low power density of 0.35 W/cm². FIG. 9 shows a comparison between use of nanoparticles with an ytterbium ratio of 20% and those with an ytterbium ratio of 80% showing that an advantage in phototherapeutic effect was obtained by increasing the ytterbium ratio from 20% to 80%. The 5-aminolevulinic acid conjugated nanoparticles with an ytterbium ratio of 20% (β-NaYF$_4$:Yb(20%),Er(2%)@β-NaYF$_4$ ALA) showed no cell killing, whereas 5-aminolevulinic acid conjugated nanoparticles as disclosed herein with an 80% ytterbium ratio (α-NaYF$_4$:Yb(80%),Er(2%)@CaF$_2$ ALA) caused more than 60% cell death after 20 min. irradiation. This is the lowest power density at which an upconverting nanoparticle photodynamic therapy agent system has been demonstrated, which can be explained by the high near infra-red-to-red upconverting efficiency achieved with the 5-aminolevulinic acid conjugated nanoparticles as disclosed herein with an 80% ytterbium ratio (α-NaYF$_4$:Yb (80%),Er(2%)@CaF$_2$).

Figure 10:
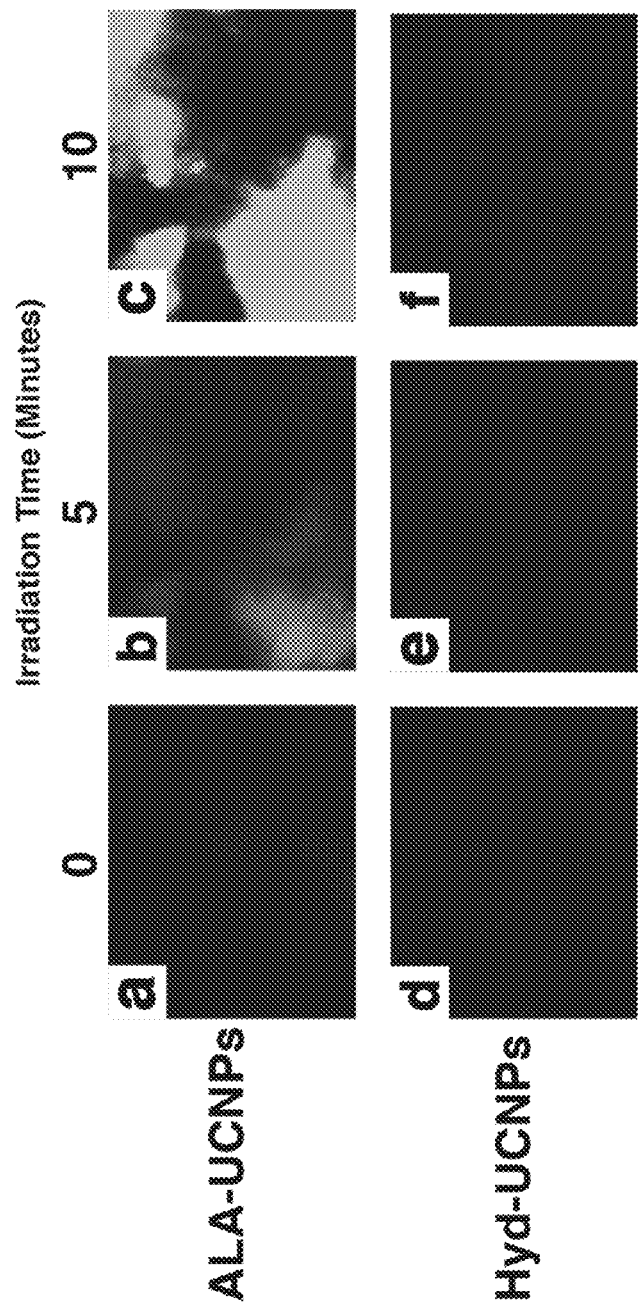
FIG. 10: Fluorescence microscopy images showing detection of singlet oxygen production by the fluorescence of DCFDA in HeLa cells exposed to 100 μg/mL of 5-aminolevulinic acid functionalized upconverting nanoparticles and irradiated with CW 980 nm light at 1 W/cm$^2$ power density for (a) 0, (b) 5 and (c) 10 min; compared with fluorescence microscopy images from a control experiment showing absence of detection of singlet oxygen production by the fluorescence of DCFDA in HeLa cells exposed to 100 μg/mL of hydrazide-functionalized upconverting nanoparticles (with no 5-ALA) for (d) 0, (e) 5 and (f) 10 min.
Figure 11:
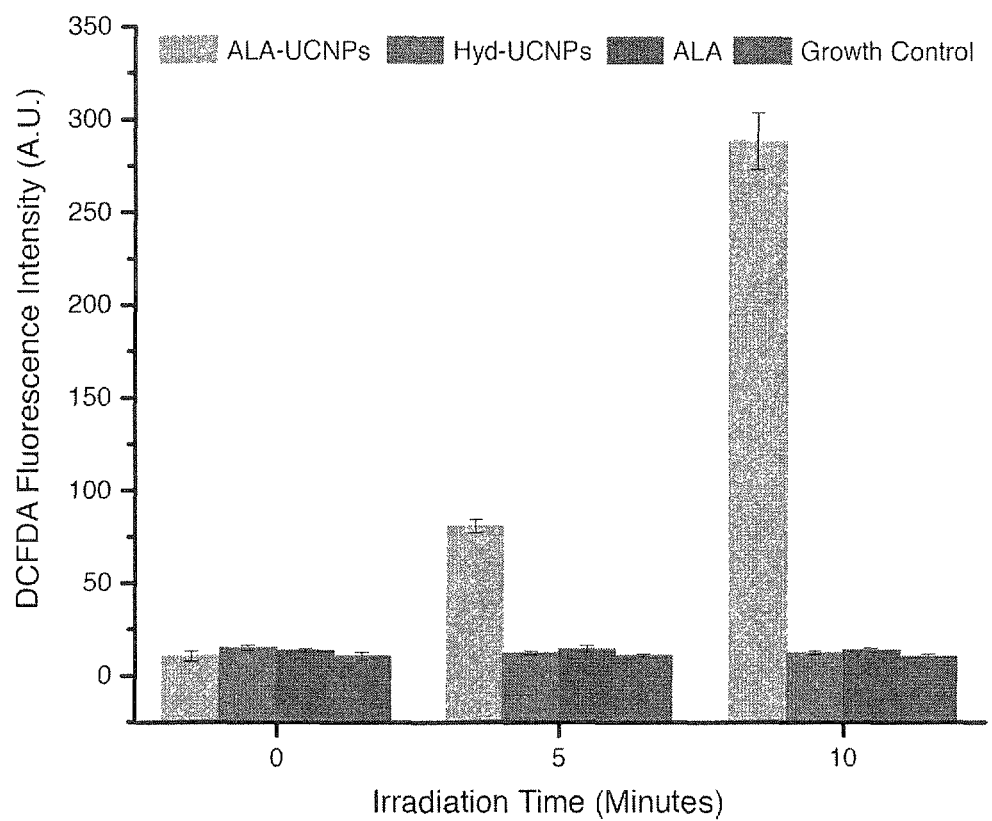
FIG. 11: Plots showing singlet oxygen in HeLa cells irradiated with CW 980 nm light at 1 W/cm$^2$ power density for irradiated cells exposed to calcium-fluoride coated upconverting nanoparticles containing 80% molar ratio ytterbium functionalized with 5-aminolevulinic acid (α-NaYF$_4$:Yb(80%),Er(2%)@CaF$_2$ ALA, 100 μg/mL and controls.

To investigate the mechanism of the results from the above mentioned experiments, cells were stained with 2',7'-dichlorofluorescein diacetate (DCFDA), a fluorescent indicator for singlet oxygen generation, and imaged using fluorescence microscopy. The results are shown in FIG. 10. When DCFDA diffuses into the cell it is acetylated into a non-fluorescent compound by cellular esterases. Reactive oxygen species (ROS) oxidize the non-fluorescent compound to 2', 7'-dichlorofluorescein (DCF), which has bright green fluorescence. FIG. 10 shows that cells exposed to 5-aminolevulinic acid-conjugated upconverting nanoparticles exhibited intensifying DCFDA fluorescence over irradiation time, indicating the production of PpIX and then singlet oxygen. See images (a), (b) and (c) of FIG. 10. In contrast, no increase in fluorescence was seen with hydrazide-functionalized nanoparticles (without 5-ALA conjugation). See images (d), (e) and (f) of FIG. 10. The data were corroborated by quantifying the singlet oxygen production by measuring the fluorescence intensity of the DCFDA using 96-well microtiter plate reader. The results of the 96-well microtiter plate measurement are shown in FIG. 11. Both DCFDA fluorescence imaging and microtiter plate measurement indicate effective prodrug delivery and subsequent PpIX activation by the red-emitting upconverting nanoparticles provided by the present disclosure.

Photodynamic therapy of a deep-set tumor condition using the 5-aminolevulinic acid conjugated upconverting nanoparticles with an 80% ytterbium ratio was simulated by placing pieces of pork tissue of varying thickness (representing a patient's flesh) between a near infra-red laser and HeLa cells exposed to the upconverting nanoparticles, as shown in FIG. 12(*a*). The cells were analyzed for cell viability using an MTT assay. The results of the study are shown in FIG. 12(*b*). After 20 min. of irradiation at 1 W/cm², for all pork thicknesses, the cells exposed the 5-aminolevulinic acid conjugated nanoparticles as disclosed herein had cell viabilities that were reduced significant to the control hydrazide-functionalized upconverting nanoparticles (Hyd-UCNPs). In the absence of pork (0 mm), cell viability was less than 20%, in the presence of 6 mm pork, cell viability was less than 50%, and even with 12 mm pork, cell viability was still reduced to below 80% compared to the control. This establishes and validates the feasibility of using upconverting nanoparticles as a near infra-red-to-red transducer for prodrug photodynamic therapy at a deep-tissue level (up to about 1 cm or greater).

Figure 13:
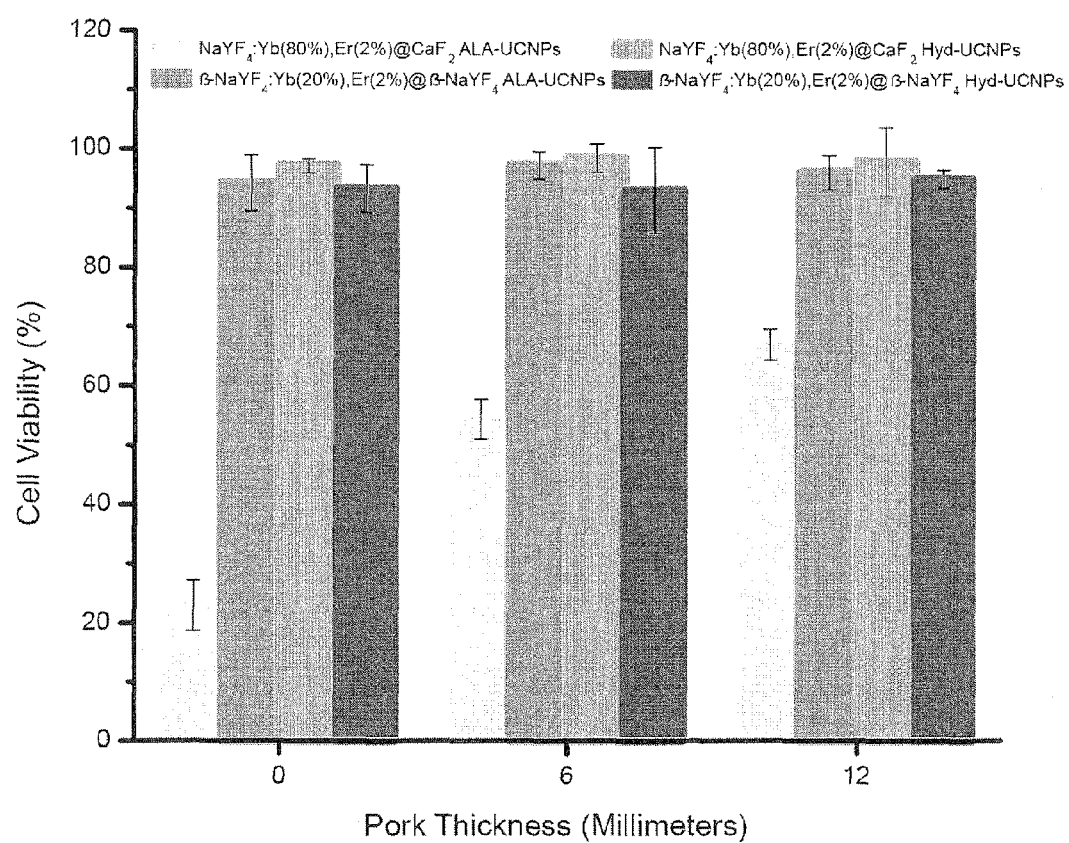
FIG. 13: Plots of HeLa cell viability for cells covered with 0, 6, and 12 mm pork tissue on top of the cells and irradiated with CW 980 nm light at a 0.35 W/cm$^2$ power density for 20 min. for cells irradiated in the presence of (i) calcium-fluoride coated upconverting nanoparticles containing 80% molar ratio ytterbium functionalized with 5-aminolevulinic acid. upconverting nanoparticles containing 20% molar ratio ytterbium functionalized with 5-aminolevulinic acid, and controls.

Finally, the red-emitting upconverting nanoparticle system containing an ytterbium ratio of 80% was compared with the known upconverting nanoparticle β/β core/shell red-emitting nanoparticles at a deep tissue level with a biocompatible low power density 0.35 W/cm² for laser irradiation. The results of the comparison are shown in FIG. 13, which demonstrates the dramatic improvement in phototherapeutic effect with the upconverting nanoparticles disclosed herein. The 5-aminolevulinic acid conjugated nanoparticles described herein having an ytterbium ratio of 80% achieved 40% cell death even through 1.2 cm of pork. The ability of the presently-disclosed lanthanide-doped upconverting nanoparticles' to induce significant phototherapeutic effect with such low power excitation yet thick superficial tissue makes it a major step forward in photodynamic therapy materials.

Formulation, Dosage Forms and Administration

When employed as therapeutically, the nanoparticles and compositions described herein can be administered in the form of pharmaceutical compositions. Thus the present disclosure provides a composition comprising a nanoparticle as described herein, or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain the nanoparticles described herein, in combination with one or more pharmaceutically acceptable carriers (excipients). In some embodiments, the composition is suitable for topical administration. In making the compositions of the invention, the nanoparticle composition is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2 wt % silicon dioxide.

The compositions can be formulated in a unit dosage form, each dosage containing from about 5 to about 1,000 mg (1 g), more usually about 100 mg to about 500 mg, of the nanoparticles. In some embodiments, each dosage contains about 10 mg of the nanoparticles. In some embodiments, each dosage contains about 50 mg of the nanoparticles. In some embodiments, each dosage contains about 25 mg of the nanoparticles. The term "unit dosage forms" refers to physically discrete units suitable as unitary dosages for human subjects and other mammals, each unit containing a predetermined quantity of nanoparticles needed to achieve the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The nanoparticles may be useful over a wide dosage range and are generally administered in a therapeutically effective amount. It will be understood, however, that the amount of the nanoparticle composition administered will usually be determined by a physician, according to the relevant circumstances, including the condition to be treated, the chosen route of administration, the particular composition being administered, the age, weight, and response of the individual patient, the severity of the patient's symptoms and the like. The therapeutic dosage can vary according to, e.g., the particular use for which the treatment is made, the manner of administration, the health and condition of the patient, and the judgment of the prescribing physician. The proportion or concentration of each component in a pharmaceutical composition can vary depending upon a number of factors including dosage, chemical characteristics (e.g., hydrophobicity), and the route of administration. For example, the nanoparticles of the invention can be provided as a suspension in an aqueous physiological buffer solution containing about 0.1 to about 10% w/v of the nanoparticles for parenteral administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, nanoparticles can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, e.g., about 0.1 to about 1000 mg of the active ingredient of the present invention.

The liquid forms in which the nanoparticles and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

For topical administration to the lung, nasal passage or airways, the nanoparticles can be formulated for inhalation or insufflation. Suitable formulations include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2, at least about 5, at least about 10, at least about 15, at least about 20, at least about 25, at least about 30, at least about 35, at least about 40, at least about 45, or at least about 50 wt % of the nanoparticles of the invention. The topical formulations can be suitably packaged in tubes of, e.g., 100 g which are optionally associated with instructions for the treatment of the select indication, e.g., psoriasis or other skin condition.

The amount of nanoparticles or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective amounts will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. The pH of the pharmaceutical preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of the nanoparticles of the present invention can vary according to, e.g., the particular use for which the treatment is made, the manner of administration of the nanoparticles, the health and condition of the patient, and the judgment of the prescribing physician. The proportion or concentration of the nanoparticles in a pharmaceutical composition can vary depending upon a number of factors including dosage and the route of administration.

EXAMPLES

The invention is further described in the following examples, which do not limit the scope of the invention described in the claims.

Materials for the following examples were $Y_2O_3$, (99.9%), $Yb_2O_3$ (99.9%), $Er_2O_3$ (99.9%), $CF_3COONa$ (99.9%), $CF_3COOH$, $CaCO_3$, 1-octadecene (90%), oleic acid (90%), oleylamine (70%), 1-ethyl-3-(3-dimethylaminopropyl) carbodiimide hydrochloride (EDC), N-hydroxysulfosuccinimide sodium salt (sulfo-NHS), poly(acrylic acid), hydrazine monohydrate, Thiazolyl Blue Tetrazolium Bromide (3-(4,5-dimethylthiazol-2-yl)-2,5-diphenyltetrazolium bromide; MTT) and 2',7'-dichlorofluorescein diacetate (DCFDA), all purchased from Sigma-Aldrich and used without further purification. 5-Aminolevulinic acid hydrochloride (98%) was purchased from AK Scientific. Nitrosonium tetrafluoroborate ($NOBF_4$) was purchased from Alfa. Lanthanide (Ln) or rare earth trifluoroacetates, $Ln(OC(O)CF_3)_3$, were prepared as described by Chatterjee, et al., Nanoparticles in Photodynamic Therapy: an Emerging Paradigm, Adv. Drug Deliv. Rev. 2008, 15, 1627.

FT-IR spectra were recorded on a Nicolet Nexus FT-IR spectrometer, using the SMART iTR™ for ATR measurements. The upconversion photoluminescence spectra were measured by a SPEX FluoroMax®-3 spectrofluorimeter (Horiba) (spectral resolution of 1 nm, emission slit of 5 nm, and integral period of 0.1 s) excited at 980 nm using a fiber-coupled laser diode introduced to the sample chamber of the spectrofluorimeter. Cells were imaged using a Nikon Eclipse TE 2000 microscope, equipped with a Nuance CCD camera capable of imaging. The light source was a fiber-coupled laser diode emitting at 980 nm, with the fiber introduced through the entrance port of the microscope. The size distribution of the samples was determined by dynamic light scattering (DLS) equipped with a Zetasizer Nano-ZS (He—Ne laser wavelength at 633 nm) and an auto-titrator (Malvern Instruments, Malvern, UK). The absorbance for the MTT experiment and the fluorescence for DCFDA staining experiment was found using a microplate reader (Molecular Devices Co., Menlo Park, Calif.). 5-ALA concentration was monitored by HPLC (Varian ProStar) for loading efficiency data.

Synthesis of Oleic Acid-Capped Ytterbium/Erbium Doped Sodium Yttrium Fluoride Coated with Calcium Fluoride α-NaYF$_4$:Yb(X%),Er(2%)@CaF$_2$ In brief, in a three-neck reaction flask, a mixture of oleic acid (8 mmol) and 1-octadecene (8 mmol) was heated to 120° C. to remove trace oxygen and water. It was subsequently heated to the thermolysis reaction temperature (310° C.) under argon. A precursor solution for an α-NaLnF$_4$ core was prepared by dispersing CF$_3$COONa (0.5 mmol) and Ln(OC(O)CF$_3$)$_3$ (0.5 mmol in total) within oleic acid (5 mmol) and 1-octadecene (5 mmol), The mol-percentage of Er(OC(O)CF$_3$)$_3$ was fixed at 2%, while Yb(OC(O)CF$_3$)$_3$ was employed in molar ratios of 20%, 40%, 60%, 80%, 98% mol-percentage for different samples (with the balance of the rare earth being yttrium in the form of Y(OC(O)CF$_3$)$_3$). After 10 min. under vacuum, the core precursor solution was injected into the reaction flask at a rate of 1 mL/min. Then the thermolysis reaction mixture was kept at 310° C. for 1 h under dry argon flow.

To coat the nanoparticles with a calcium fluoride shell, Ca(OC(O)CF$_3$)$_2$ (2.000 mmol), oleic acid (5 mmol), and 1-octadecene (5 mmol) was mixed and 10 min. vacuum degassed to make a shell precursor solution. An equal volume solution was injected into the reaction mixture twice with an equal volume, followed by 30 min. reaction at 310° C. after each injection. The reaction mixture was cooled and α-NaLnF$_4$@CaF$_2$ upconverting nanoparticles (UCNPs) were precipitated by adding EtOH to the cooled reaction flask. The nanoparticles were then washed by centrifugal washing twice with EtOH. The resulting white powders were re-dispersed in 10 mL hexane for further use.

Synthesis of Polyacrylic Acid Coated Upconverting Nanoparticles α-NaYF$_4$:Yb,Er(2%)@CaF$_2$ PAA-UCNPs In a process modified from that described by Zhao, et al., Stem Cell Labeling using Polyethylenimine Conjugated (α-NaYbF4:Tm$^{3+}$)/CaF$_2$ Upconversion Nanoparticles, *Theranostics*, 2013, 3, 249, 10 mg of oleic acid-capped UCNPs (prepared as described above or by analogous methods) were dispersed in hexane and mixed with 0.20 g of nitrosonium tetrafluoroborate dissolved in DMF in a sealed vial overnight. Subsequently, UCNPs were precipitated with isopropanol and centrifugally washed once in DMF. UCNPs dissolved in DMF were mixed with 10 mg of poly(acrylic acid) dissolved in DMF at 80° C. overnight. UCNPs were then precipitated with IPA and centrifugally washed twice in water.

Synthesis of Hydrazide Functionalized Upconverting Nanoparticles α-NaYF$_4$:Yb,Er(2%)@CaF$_2$ Hyd-UCNPs PAA-UCNPs dissolved in PBS at 1 mg/mL were exposed to 50 mg of EDC and 10 mg of sulfo-NHS for 4 h. Then, excess EDC and sulfo-NHS were washed off by centrifugation and carboxyl-activated PAA-UCNPs were re-dispersed in PBS. This dispersion was mixed with 5 mL of hydrazine monohydrate overnight and subsequently centrifugally washed several times in deionized water.

Synthesis of 5-Aminolevulinic Acid Functionalized Upconverting Nanoparticles α-NaYF$_4$:Yb,Er(2%)@CaF$_2$ ALA-UCNPs Hyd-UCNPs were centrifugally washed into 10 mL anhydrous MeOH several times at 1 mg/mL. 5 mL of 5-aminolevulinic acid dissolved in anhydrous MeOH was added at 10 mg/mL followed by a drop of dilute AcOH for catalysis were and the mixture was maintained at ambient temperature for 48 h. The resulting 5-aminolevulinic acid functionalized upconverting nanoparticles (ALA-UCNPs) were then centrifugally washed and dispersed in PBS at 5 mg/mL.

Synthesis of β-NaYF$_4$:Yb(20%),Er(2%)@β-NaYF$_4$

β-NaYF$_4$:Yb,Er@β-NaYF$_4$ Core-Shell UCNPs were prepared using a modified three-step thermolysis method. In the first step, the CF$_3$COONa (0.5 mmol) and Ln(OC(O)CF$_3$)$_3$ precursors (0.5 mmol in total, in a molar ratio of 78% Y, 20% Yb, 2% Er) were mixed with oleic acid (5 mmol), oleyl amine (5 mmol) and 1-octadecene (10 mmol) in a two-neck reaction flask. The slurry mixture was heated to 110° C. to form a transparent solution. The resulting solution was then degassed for 10 min. to remove the oxygen and water. The flask was then heated to 300° C. at a rate of 15° C./min under dry argon flow, and remained at 300° C. for 30 min. The α-NaLnF$_4$ intermediate UCNPs were acquired by cooling down the reaction mixture to room temperature, followed by centrifugation with EtOH.

In a second step, the α-NaYF$_4$: 20% Yb, 2% Er UCNPs were re-dispersed in oleic acid (10 mmol) and 1-octadecene (10 mmol) along with CF$_3$COONa (0.5 mmol) in a two-neck flask. After degassing at 110° C. for 10 min., the flask was heated to 325° C. at a rate of 15° C./min under dry argon flow, and remained at 325° C. for 30 min. The β-NaYF$_4$:20% Yb, 2% Er UCNPs were then centrifugally separated from the cooled reaction media and suspended in 10 mL of hexane as the stock solution for further use.

In a third step, the as-synthesized α-NaYF4: 20% Yb, 2% Er UCNPs served as crystallization seeds for the epitaxial growth of an undoped α-NaYF$_4$ shell. A stock solution of suspended α-NaYF4: 20% Yb, 2% Er UCNPs (5 mL, ca. 0.26 μmol/L core UCNPs) was transferred into a two-neck flask and hexane was sequentially removed by heating. Then CF$_3$COONa (0.5 mmol) and Y(OC(O)CF$_3$)$_3$ (0.5 mmol) were introduced as UCNP shell precursors with oleic acid (10 mmol) and 1-octadecene (10 mmol). After 10 min. of degassing at 110° C., the flask was heated to 325° C. at a rate of 15° C./min. under dry argon flow and the reaction mixture was kept at 325° C. for 30 min. The reaction mixture was allowed to cool and the product was precipitated by adding EtOH to the cooled reaction flask. After centrifugal washing with hexane/EtOH, the core/shell UCNPs were re-dispersed in 10 mL of hexane for further use.

Cell Viability Analysis by MTT Assay

A 96-well microtiter plate seeded with 1×10$^4$ HeLa cells/well was incubated overnight at 37° C. with 5% CO$_2$. Cells were subsequently exposed to (i) 5-aminolevulinic acid functionalized upconverting nanoparticles comprising 80 mol % ytterbium (ALA-UCNPs, 100 μg/mL), (ii) hydrazide functionalized upconverting nanoparticles (no 5-ALA) (Hyd-UCNPs, 100 μg/mL), (iii) free 5-aminolevulinic acid (ALA, 100 μg/mL) or (iv) PBS (growth medium control) and then irradiated with CW 980 nm laser diode at 1 W/cm$^2$ for 0, 5, 10, or 20 min. After overnight incubation, cells were labeled with 12 mM solution of MTT in PBS for 4 h. Finally, the media was aspirated and replaced with 50 μL DMSO and cell viability was quantified by formazan absorption determined by a plate reader at 540 nm. The results are shown in FIG. 8.

Singlet Oxygen Detection Cell Imaging

Glass-bottom confocal dishes seeded with $1\times10^6$ HeLa cells were incubated overnight at 37° C. with 5% $CO_2$. Cells were subsequently exposed to 100 µg/mL of 5-aminolevulinic acid functionalized upconverting nanoparticles (ALA-UCNPs) or hydrazide functionalized upconverting nanoparticles (Hyd-UCNPs) for 4 h. Cells were washed three times with warmed HBSS and then stained with 25 µM DCFDA in HBSS for 45 min. Using a fluorescent microscope equipped with a CW 980 nm laser diode at 1 W/cm², DCFDA fluorescence was imaged with 495 nm excitation and 535 nm emission for 0, 5, and 10 min. of irradiation using a 60× water-immersion objective lens. The results are shown in FIG. 10.

Singlet Oxygen Detection Quantification

A 96-well microtiter plate seeded with $1\times10^4$ HeLa cells/well was incubated overnight at 37° C. with 5% $CO_2$. Cells were subsequently exposed to (i) calcium-fluoride coated upconverting nanoparticles containing 80% molar ratio ytterbium functionalized with 5-aminolevulinic acid ($\alpha$-NaYF$_4$:Yb(80%),Er(2%)@CaF$_2$ ALA, 100 µg/mL) (ALA-UCNPs), (ii) calcium-fluoride coated upconverting nanoparticles containing 80% molar ratio ytterbium functionalized by hydrazide (no 5-ALA) ($\alpha$-NaYF$_4$:Yb(80%),Er(2%)@CaF$_2$ Hyd, 100 µg/mL) (Hyd-UCNPs), (iii) 5-aminolevulinic acid (100 µg/mL) or (iv) phosphate buffered saline only (growth medium control). The cells were then stained with 25 µM DCFDA in HBSS for 45 min. After irradiation with CW 980 nm laser diode at 1 W/cm² for 0, 5, or 10 min., DCFDA fluorescence was immediately determined with a plate reader with 495 nm excitation and 535 nm emissions. The results are shown in FIG. 11.

In Vivo Deep Tumor Photodynamic Therapy Treatment

In vivo testing was conducted in subcutaneous tumors grown on Balb/c mice models to evaluate the effect of photodynamic therapy treatment using the upconversion nanoparticles described herein. The tumor volume reduction effect of a red light laser ranging from ~635-685 nm (PpIX's activation region) and 980 nm light irradiation (activation wavelength of the upconverting nanoparticles described herein) was compared at a biocompatible level of 0.5 W/cm².

Female Balb/c mice were purchased from Nanjing Peng Sheng Biological Technology Co. Ltd. and used under protocols approved by Soochow University Laboratory Animal Center. 4T1 cells ($1\times10^6$) suspended in 40 µL of PBS were subcutaneously injected into the back of each female Balb/c mouse. After about 6 days, the mice bearing 4T1 tumors were treated when the tumor volume reached about 50 mm³. The mice were divided into 9 groups (n=5 per group) and intratumorally injected with about 40 µL of saline of calcium-fluoride coated upconverting nanoparticles containing 80% molar ratio ytterbium functionalized with 5-aminolevulinic acid ($\alpha$-NaYF$_4$:Yb(80%),Er(2%)@CaF$_2$ ALA) (ALA-UCNPs) (20 mg/mL).

An optical fiber-coupled 980 nm high power laser diode (Hi-Tech Optoelectronics Co., Ltd. Beijing, China) was used to irradiate tumors at a power density of about 0.5 W/cm² for 40 min. (1 min. interval after each minute of irradiation). The tumor sizes were measured by a caliper every other day and calculated as the volume (tumor length)×(tumor width)²/2. The body weight of mice was also measured with every tumor measurement and percent change was calculated by the formula (observed body weight)/(body weight on day 0)×100%.

Figure 14A:
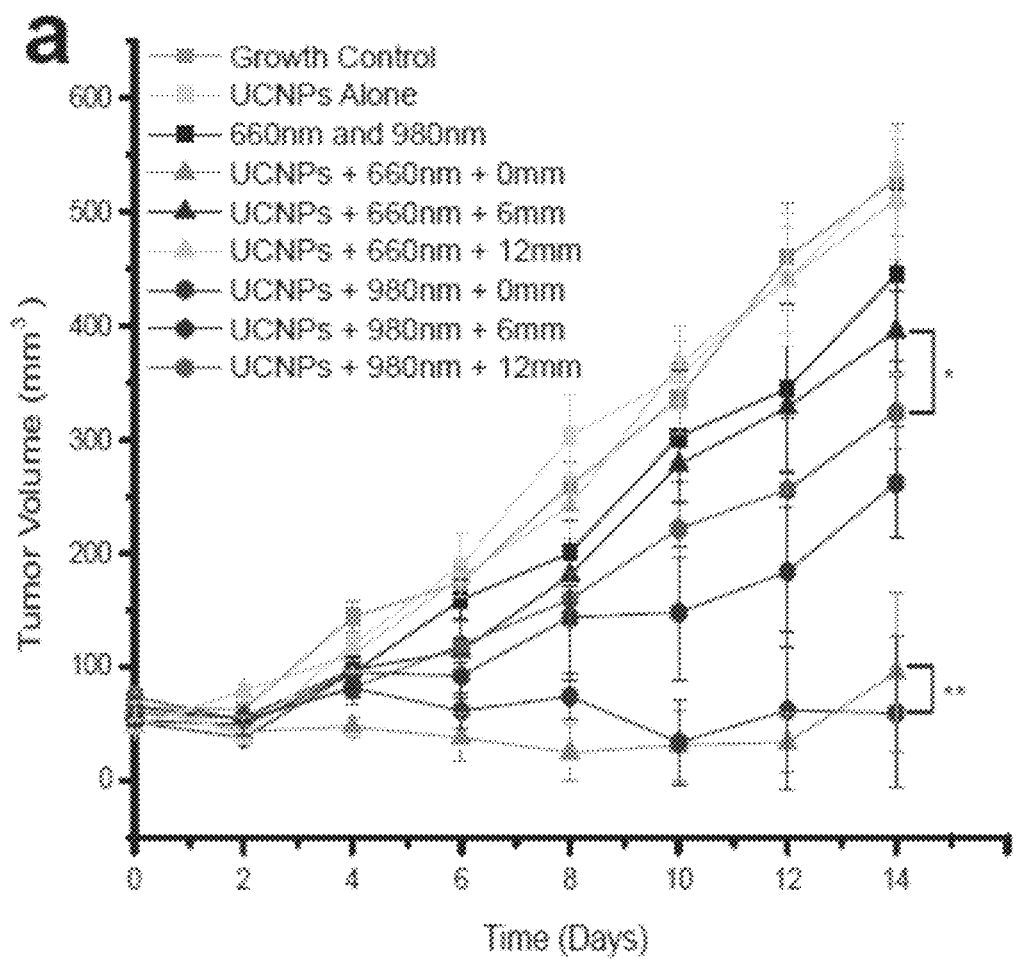
FIG. 14A: Plots of the in vivo volume of tumors exposed to various controls and 5-aminolevulinic acid conjugated UCNPs with red and near-infrared irradiation (0.5 W/cm$^2$) in simulated deep tumors together with controls.
Figure 14B:
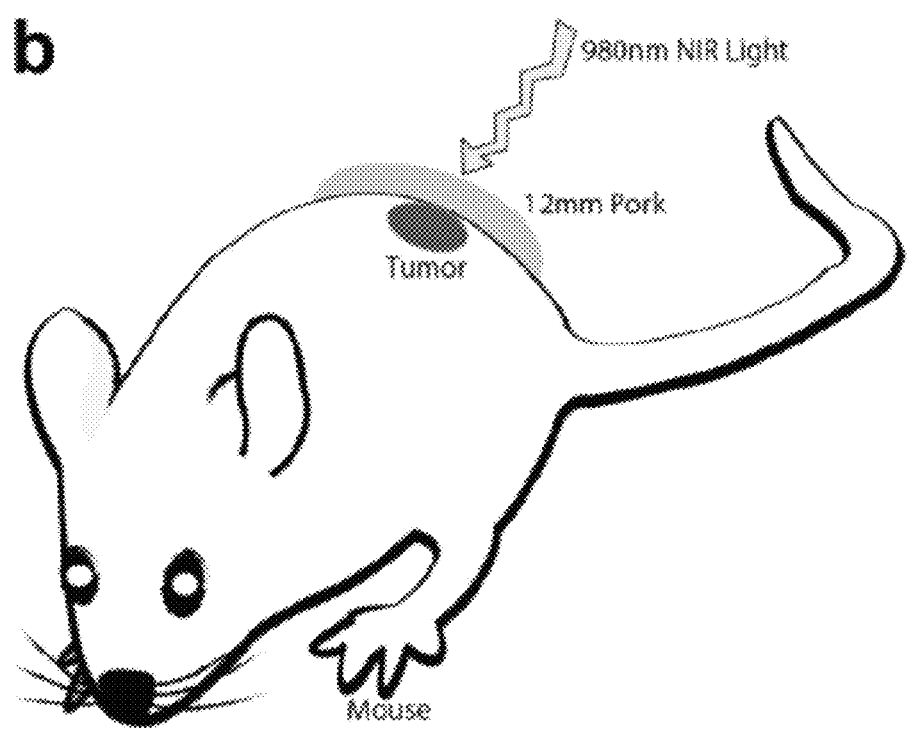
FIG. 14B: is a diagram of in vivo photodynamic therapy treatment with red or near infra-red light conducted inserting pork tissue between the laser and the mice tumors to simulate treatment of deep tumors.

The results are shown in FIG. 14. FIG. 14(a) is a plot of tumor volume versus time for animals treated in each group. FIG. 14(a) shows that there was no statistically significant difference between treatment with NIR (lowest hexagon curve on the plot) and red (lowest triangle curve on the plot) light, indicating the upconverting nanoparticle/photodynamic therapy system described herein can compete with the clinical norm using red light. However, the advantage of 980 nm light is evident when PDT treatment was conducted inserting pork tissue between the laser and the mice tumors (as shown in FIG. 14(b)) to simulate treatment of deep tumors. In this case, irradiation in the presence of 5-ALA-functionalized UCNPs with 980 nm light irradiation produced about 150 mm³ tumor reduction even with 6 or 12 mm of pork tissue above the tumor (third and fourth lowest curves, respectively), while there was no noticeable therapeutic effect with clinically used red light irradiation at that depth (top triangle curve, which was similar to controls). Moreover, statistical significance tests reveal that even with thick 12 mm layer of superficial tissue (pork), the 980 nm light induced therapy that is significantly more effective than the tumor reduction induced by red light with 6 mm of superficial tissue as shown by the upper bracket in FIG. 14(a).

Figure 15:
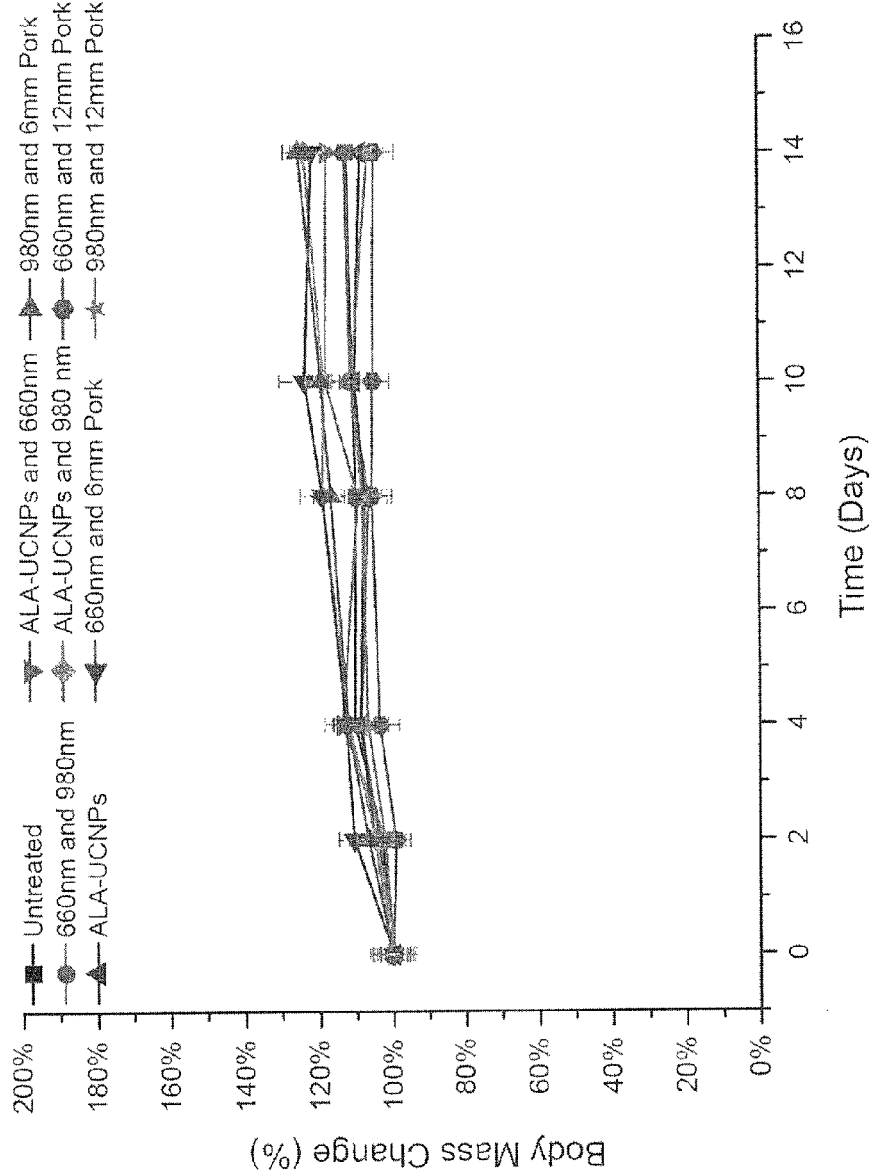
FIG. 15 is a plot of body mass change of mice in in vivo PDT treatment groups with upconverting nanoparticles and controls after 14 days, with the lack of significant difference between the groups showing absence of toxicity.

FIG. 15 shows a plot of body mass change for control and treatment groups with no significant difference across the groups indicating lack of noticeable toxicity.

5-Aminolevulinic Acid Loading Efficiency Determination Using High Performance Liquid Chromatography (HPLC)

After the 5-aminolevulinic acid conjugation process and centrifugation of fresh ALA-UCNPs, the MeOH-based supernatant was saved and vacuum dried, and leftover solutes (including the un-conjugated ALA) were re-dispersed in 2 mL of deionized waster. This solution was analyzed by HPLC to determine the concentration of free 5-ALA using a standard calibration curve (264 nm detection wavelength), and back-calculation was used to determine the amount of ALA conjugated to the hydrazide functionalized UCNPs.

CAPTIONS DESCRIBING THE FIGURES

FIGS. 1(a) and 1(b). FIG. 1(a): Emission spectra (a) under CW 980 nm 1 W/cm² excitation of $\alpha$-NaYF$_4$:Yb,Er@CaF$_2$ UCNPs with different Yb-levels from 20 to 98%—increased levels of Yb lead to increased fluorescence. FIG. 1(b): Integrated counts of red-emission and photographs (inset) of $\alpha$-NaYF$_4$:Yb,Er@CaF$_2$ UCNPs with different Yb-levels from 20 to 98%.

Figure 2:
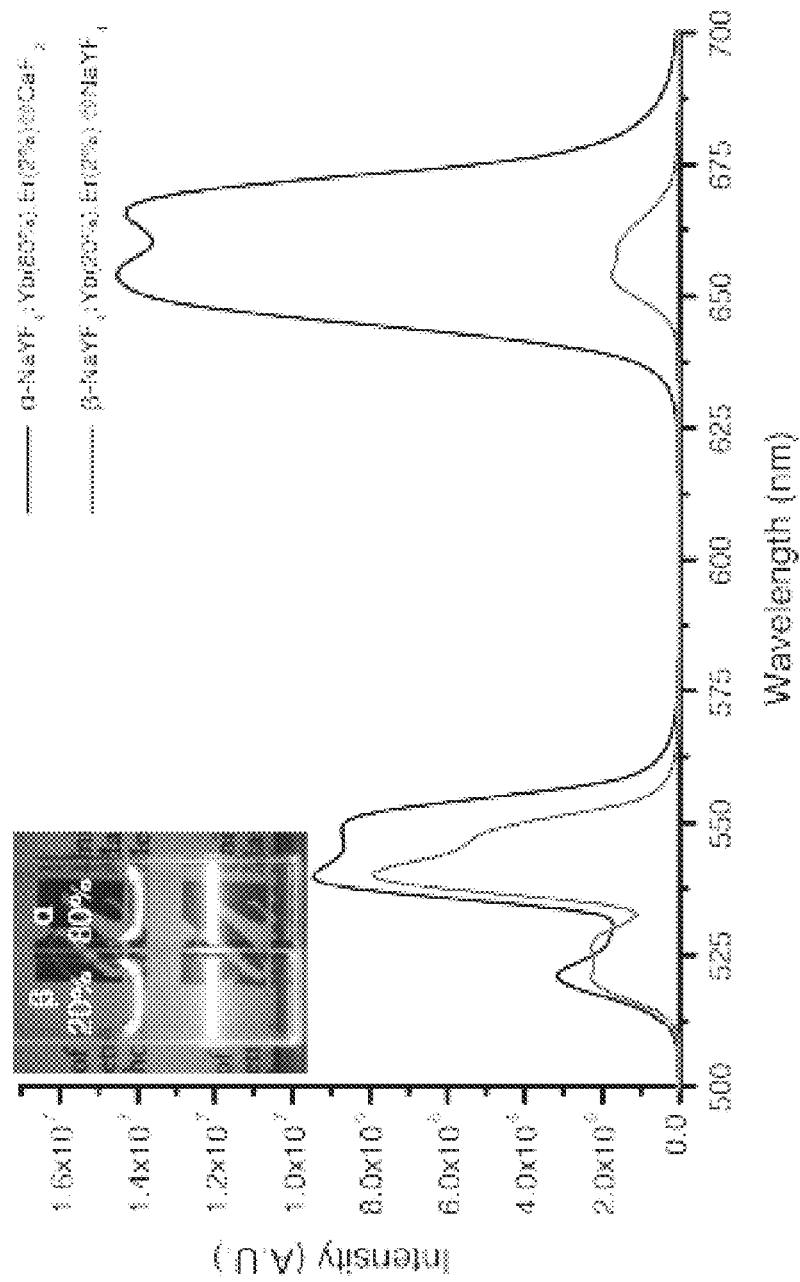
FIG. 2: Emission spectra and photograph (inset) of calcium fluoride coated upconverting nanoparticles with 80% molar ratio of ytterbium, and upconverting nanoparticles with 20% molar ratio of ytterbium showing higher emission for the nanoparticles containing 80% molar ratio of ytterbium.

FIG. 2: Emission spectra and photograph (inset) of calcium fluoride coated upconverting nanoparticles with 80% molar ratio of ytterbium, $\alpha$-NaYF$_4$:Yb(80%),Er(2%)@CaF$_2$ (optimal red emissions), and upconverting nanoparticles with 20% molar ratio of ytterbium $\beta$-NaYF$_4$:Yb(20%),Er(2%)@$\beta$-NaYF$_4$, showing higher emission for $\alpha$-NaYF$_4$:Yb(80%),Er(2%)@CaF$_2$.

FIGS. 3(a), 3(b) and 3(c): FIGS. 3(a), 3(b): TEM images of (a) uncoated upconverting nanoparticles containing an 80% molar ratio of ytterbium, $\alpha$-NaYF$_4$:Yb(80%),Er(2%) and (b) calcium fluoride coated upconverting nanoparticles containing an 80% molar ratio of ytterbium, $\alpha$-NaYF$_4$:Yb (80%),Er(2%)@CaF$_2$. FIG. 3(c): Size distributions of the uncoated and coated upconverting nanoparticles (left peak—uncoated; right peak CaF$_2$ coated).

FIG. 4: Plot of the power dependence of red emission fluorescence from calcium fluoride coated upconverting nanoparticles containing an 80% molar ratio of ytterbium α-NaYF$_4$:Yb (80%),Er(2%)@CaF$_2$ UCNPs, with the slope of 1.6 indicating that the fluorescence results from a two-photon process.

FIG. 5: Diagram illustrating the process of conjugating 5-aminolevulinic acid (5-ALA or ALA) to upconverting nanoparticles UCNPs via a pH-responsive hydrazone linkage.

FIG. 6: Plot showing the size distributions of polyacrylic acid coated upconverting nanoparticles (PAA-UCNPs), hydrazide functionalized upconverting nanoparticles (Hyd-UCNPs), and 5-aminolevulinic acid functionalized upconverting nanoparticles (ALA-UCNPs) by number as determined by dynamic light scattering in PBS.

FIGS. 7(a), (b), (c), (d), and (e). FIGS. 7(a)-(c) are TEM images of (a) polyacrylic acid coated upconverting nanoparticles (PAA-UCNPs), (b) hydrazide functionalized upconverting nanoparticles (Hyd-UCNPs), and (c) 5-aminolevulinic acid functionalized upconverting nanoparticles (ALA-UCNPs). FIGS. 7(d) and (e): FT-IR spectra of polyacrylic acid coated upconverting nanoparticles (PAA-UCNPs), hydrazide functionalized upconverting nanoparticles (Hyd-UCNPs), and 5-aminolevulinic acid functionalized upconverting nanoparticles (ALA-UCNPs). FIG. 7(d) shows the full spectra and FIG. 7(e) shows partial, detailed spectra.

FIG. 8: Plots showing the viability of HeLa cells irradiated with CW 980 nm light at 1 W/cm$^2$ power density. From left to right at each time point are plots representing cell viability observed when irradiation was carried out in the presence of (i) 5-aminolevulinic acid functionalized upconverting nanoparticles (ALA-UCNPs, 100 µg/mL), (ii) hydrazide functionalized upconverting nanoparticles (Hyd-UCNPs, 100 µg/mL), (iii) free 5-aminolevulinic acid (ALA, 100 µg/mL) and (iv) PBS (growth medium control).

FIG. 9: Plots showing the viability of HeLa cells irradiated with CW 980 nm light at 0.35 W/cm$^2$ power density. From left to right at each time point are plots representing cell viability observed when irradiation was carried out in the presence of (i) calcium-fluoride coated upconverting nanoparticles containing 80% molar ratio ytterbium functionalized with 5-aminolevulinic acid (α-NaYF$_4$:Yb(80%), Er(2%)@CaF$_2$ ALA, 100 µg/mL), (ii) upconverting nanoparticles containing 20% molar ratio ytterbium functionalized with 5-aminolevulinic acid (β-NaYF$_4$:Yb (20%),Er(2%)@β-NaYF$_4$ ALA, 100 µg/mL), (iii) hydrazide-functionalized calcium-fluoride coated upconverting nanoparticles containing 80% molar ratio ytterbium (no 5-ALA) (α-NaYF$_4$:Yb(80%),Er(2%)@CaF$_2$ Hyd, 100 µg/mL), and (iv) hydrazide-functionalized upconverting nanoparticles containing 20% molar ratio ytterbium (no 5-ALA) (β-NaYF$_4$:Yb(20%),Er(2%)@β-NaYF$_4$ Hyd, 100 µg/mL).

FIGS. 10(a), 10(b), 10(c), 10(d), 10(e) and 10(f). Fluorescence microscopy images showing detection of singlet oxygen production in cells by the fluorescence of DCFDA. FIGS. 10(a), 10(b), 10(c): Fluorescence microscopy images showing detection of singlet oxygen production by the fluorescence of DCFDA in HeLa cells exposed to 100 µg/mL of 5-aminolevulinic acid functionalized upconverting nanoparticles (α-NaYF$_4$:Yb(80%),Er(2%)@CaF$_2$ ALA, 100 µg/mL) and irradiated with CW 980 nm light at 1 W/cm$^2$ power density for (a) 0, (b) 5 and (c) 10 min FIGS. 10(d), 10(e), 10(f): Fluorescence microscopy images from a control experiment showing absence of detection of singlet oxygen production by the fluorescence of DCFDA in HeLa cells exposed to 100 µg/mL of hydrazide-functionalized upconverting nanoparticles (no 5-ALA) (α-NaYF$_4$:Yb(80%),Er (2%)@CaF$_2$ Hyd, 100 µg/mL) and irradiated with CW 980 nm light at 1 W/cm$^2$ power density for (d) 0, (e) 5 and (f) 10 min.

FIG. 11: Plots showing singlet oxygen in HeLa cells irradiated with CW 980 nm light at 1 W/cm$^2$ power density. From left to right at each time point are plots showing the DCFDA fluorescence intensity for irradiated cells exposed to (i) calcium-fluoride coated upconverting nanoparticles containing 80% molar ratio ytterbium functionalized with 5-aminolevulinic acid (α-NaYF$_4$:Yb(80%),Er(2%)@CaF$_2$ ALA, 100 µg/mL), (ii) calcium-fluoride coated upconverting nanoparticles containing 80% molar ratio ytterbium functionalized hydrazide (no 5-ALA) (α-NaYF$_4$:Yb(80%),Er (2%)@CaF$_2$ Hyd, 100 µg/mL), (iii) 5-aminolevulinic acid (100 µg/mL) or (iv) PBS (controls in growth medium only).

Figures 12A, 12B:
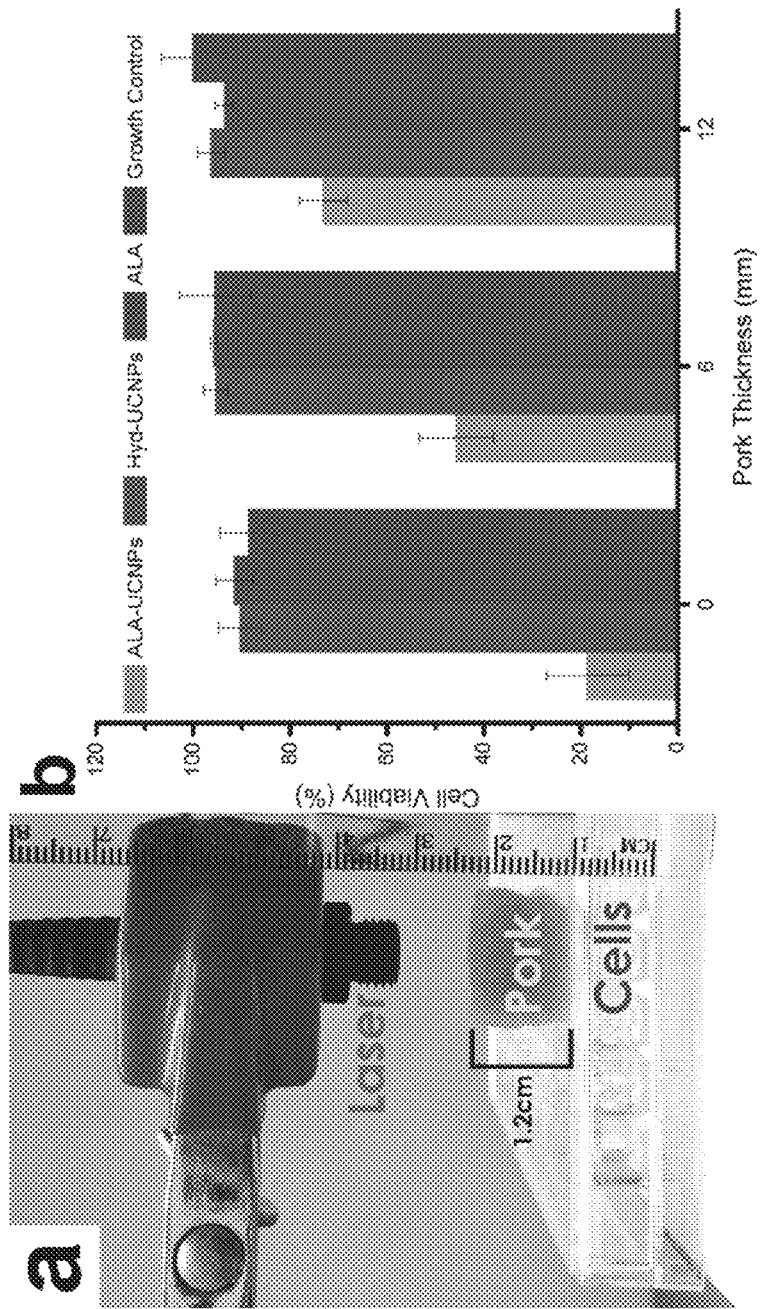
FIG. 12: (a) Photograph of the setup for simulated photodynamic therapy using an in vitro MTT assay; and (b) plots of HeLa cell viability for cells covered with 0, 6, and 12 mm pork tissue on top of the cells and irradiated with CW 980 nm light at a 1 W/cm$^2$ power density for 20 for cells irradiated in the presence of calcium-fluoride coated upconverting nanoparticles containing 80% molar ratio ytterbium functionalized with 5-aminolevulinic acid and controls.

FIGS. 12(a) and 12(b): FIG. 12(a) Photograph of the setup for simulated photodynamic therapy using an in vitro MTT assay. FIG. 12(b): Plots of HeLa cell viability for cells covered with 0, 6, and 12 mm pork tissue on top of the cells and irradiated with CW 980 nm light at a 1 W/cm$^2$ power density for 20 min. From left to right at each pork thickness are plots of cell viability for cells irradiated in the presence of (i) calcium-fluoride coated upconverting nanoparticles containing 80% molar ratio ytterbium functionalized with 5-aminolevulinic acid (α-NaYF$_4$:Yb(80%),Er(2%)@CaF$_2$ ALA, 100 µg/mL), (ii) calcium-fluoride coated upconverting nanoparticles containing 80% molar ratio ytterbium functionalized hydrazide (no 5-ALA) (α-NaYF$_4$:Yb(80%),Er (2%)@CaF$_2$ Hyd, 100 µg/mL), (iii) 5-aminolevulinic acid (100 µg/mL) or (iv) nothing (controls in growth medium only).

FIG. 13: Plots of HeLa cell viability for cells covered with 0, 6, and 12 mm pork tissue on top of the cells and irradiated with CW 980 nm light at a 0.35 W/cm$^2$ power density for 20 min. From left to right at each pork thickness are plots of cell viability for cells irradiated in the presence of (i) calcium-fluoride coated upconverting nanoparticles containing 80% molar ratio ytterbium functionalized with 5-aminolevulinic acid (α-NaYF$_4$:Yb(80%),Er(2%)@CaF$_2$ ALA, 100 µg/mL), (ii) upconverting nanoparticles containing 20% molar ratio ytterbium functionalized with 5-aminolevulinic acid (β-NaYF$_4$:Yb(20%),Er(2%)@β-NaYF$_4$ ALA, 100 µg/mL), (iii) hydrazide-functionalized calcium-fluoride coated upconverting nanoparticles containing 80% molar ratio ytterbium (no 5-ALA) (α-NaYF$_4$:Yb(80%),Er(2%)@CaF$_2$ Hyd, 100 µg/mL), and (iv) hydrazide-functionalized upconverting nanoparticles containing 20% molar ratio ytterbium (no 5-ALA) (β-NaYF$_4$:Yb(20%),Er(2%)@β-NaYF$_4$ Hyd, 100 µg/mL).

FIGS. 14(a) and 14(b). FIG. 14(a): Plots of the in vivo volume of tumors exposed to various controls and ALAUCNPs with red and near-infrared irradiation (0.5 W/cm$^2$) in simulated deep tumors. Legend: gray square, untreated tumors serving as growth controls; light gray square, tumors exposed to calcium-fluoride coated upconverting nanoparticles containing 80% molar ratio ytterbium functionalized with 5-aminolevulinic acid (α-NaYF$_4$:Yb(80%),Er(2%) @CaF$_2$ ALA) (ALA-UCNPs) and no irradiation; black square, tumors simultaneously exposed to red and near infra-red light, both at 0.5 W/cm$^2$, but no ALA-UCNPs); triangles: tumors exposed to ALA-UCNPs and clinically used red light with no pork, 6 mm pork, or 12 mm pork— tumor growth was higher as thickness of pork increased; hexagons: tumors exposed to ALA-UCNPs and deep-penetrating 980 nm light with no pork, 6 mm pork, or 12 mm pork—tumor growth was higher as thickness of pork increased, but treatment was more effective with 980 nm light as compared with red light. Statistical significance was determined from one-way t tests; significance (*) was based on $p<0.05$ and $p>0.05$ for not significant (**) pairs. There was no statistical difference between treatments with ALA-UCNPs with no pork whether red or near infra-red light was used. Treatment with ALA-UCNPs with near infra-red light was more effective than red light when pork was used. FIG. 14(b) is a diagram of in vivo photodynamic therapy treatment with red or near infra-red light conducted inserting pork tissue between the laser and the mice tumors to simulate treatment of deep tumors.

FIG. 15 is a plot of body mass change of mice in in vivo PDT treatment groups with UCNP and light exposure after 14 days. Legend: Black Square—Untreated tumors serving as growth controls; Upwards Triangle—Tumors exposed to 5-ALA-functionalized UCNPs and no irradiation; Circle—Tumors simultaneously exposed to red and near infra-red light at 0.5 $W/cm^2$ each, but no 5-ALA-functionalized UCNPs; Downwards Triangle—Tumors exposed to 5-ALA-functionalized UCNPs and clinically used red light; Left Triangle—Tumors 6 mm deep exposed to 5-ALA-functionalized UCNPs and red light; Hexagon—Tumors 12 mm deep exposed to 5-ALA-functionalized UCNPs and red light; Diamond—Tumors exposed to 5-ALA-functionalized UCNPs and deep-penetrating 980 nm light; Right Triangle—Tumors 6 mm deep exposed to 5-ALA-functionalized UCNPs and deep-penetrating 980 nm light; Star—Tumors 12 mm deep exposed to 5-ALA-functionalized UCNPs and deep-penetrating 980 nm light.

REFERENCES

1. D. K. Chatterjee, et al., *Adv. Drug Del. Rev.*, 2008, 60, 1627-1637.
2. D. E. J. G. J. Dolmans, et al., *Nat. Rev. Cancer*, 2003, 3, 380-387.
3. J. F. Lovell, et al., *Chem. Rev.*, 2010, 110, 2839-2857.
4. I. J. Macdonald, et al., *J. Porphyrins Phthalocyanines*, 2001, 5, 105-129.
5. A. Borgatti-Jeffreys; et al., *Am. J. Vet. Res.*, 2007, 68, 399-404.
6. H. Kato; et al., *Lung Cancer*, 2003, 42, 103-111.
7. S. Collaud, et al., *Current Medicinal Chemistry-Anti-Cancer Agents*, 2004, 4, 301-316.
8. T. J. Dougherty, et al., *J. Natl. Cancer Inst.*, 1998, 90, 889-905.
9. Z. Huang, *Technol. Cancer Res. Treat.*, 2005, 4, 283.
10. Q. Peng, et al., *Photochem. Photobiol.*, 1997, 65, 235-251.
11. Q. Peng, et al., *Cancer*, 1997, 79, 2282-2308.
12. M. B. Ericson, et al., *Eur. Radiol.*, 2003, 13, 195-208.
13. M. A. Oar, et al., *Chem. Mater.*, 2005, 17, 2267-2275.
14. S. Wang, et al., *J. Mater. Chem.*, 2004, 14, 487-493.
15. M. Haase, et al., *Angew. Chem. Int. Ed. Engl.*, 2011, 50, 5808-5829.
16. W. Feng, et al., *Adv. Mater.*, 2013, 25, 5287-5303.
17. F. Wang, et al., *Analyst*, 2010, 135, 1839-1854.
18. F. Wang, X. Liu, *Chem. Soc. Rev.*, 2009, 38, 976-989.
19. C. Wang, et al., *Biomaterials* 2011, 32, 6145-6154.
20. N. M. Idris, et al., *Nat. Med.*, 2012, 18, 1580-U190.
21. D. K. Chatterjee, et al., *Nanomedicine*, 2008, 3, 73-82.
22. N. M. Idris, et al., *Nat. Med.*, 2012, 18, 1580.
23. K. Liu, et al., *ACS Nano*, 2012, 6, 4054-4062.
24. J. Shan, et al., *Adv. Funct. Mater.*, 2011, 21, 2488-2495.
25. C. Wang, et al., *Biomaterials*, 2011, 32, 6145-6154.
26. H. S. Qian, et al., *Small*, 2009, 5, 2285-2290.
27. C. Wang, et al., *Biomaterials*, 2011, 32, 1110-1120.
28. G. Tian, et al., *Small*, 2013, 9, 1929-1938.
29. G. Tian, et al., *Adv. Mater.*, 2012, 24, 1226-1231.
30. X. Teng, et al., *J. Am. Chem. Soc.*, 2012, 134, 8340-8343.
31. Y. Ding, et al., *Nanoscale*, 2013, 5, 11928-11932.
32. J.-C. Boyer, et al., *Nanoscale*, 2010, 2, 1417-1419.
33. K. W. Krämer, et al., *Chem. Mater.*, 2004, 16, 1244-1251.
34. Y.-F. Wang, et al., *Chemistry—A European Journal*, 2012, 18, 5558-5564.
35. G. Chen, et al., *ACS Nano*, 2012, 6, 8280-8287.
36. X.-F. Qiao, et al., *Nanoscale*, 2012, 4, 4611-4623.
37. J. Shen, et al., *Small*, 2013, 9, 3213-3217.
38. F. Wang, et al., *Nat. Mater.*, 2011, 10, 968-973.
39. F. Wang, et al., *J. Am. Chem. Soc.*, 2008, 130, 5642-5643.
40. J. Wang, et al., *Nat. Mater.*, 2014, 13, 157-162.
41. H. L. Wen, et al., *Angew. Chem., Int. Ed.* 2013, 52, 13419-13423.
42. Y. Dai, et al., *Biomaterials*, 2012, 33, 8704-8713.
43. G. Chen, et al., *Chem. Rev.*, 2014, 114, 5161-5214.
44. P. Bilski, et al., *Free Radical Biol. Med.*, 2002, 33, 938-946.
45. L. Zhao, et al., *Theranostics*, 2013, 3, 249-257.
46. A. Punjabi, et al., *ACS Nano*, 2014, 8(10), 10621-10630 and supplementary material.

Other Embodiments

It is to be understood that while the invention has been described in conjunction with the detailed description thereof, the foregoing description is intended to illustrate and not limit the scope of the invention, which is defined by the scope of the appended claims. A number of embodiments of the invention have been described. Nevertheless, it will be understood that various modifications may be made without departing from the spirit and scope of the invention. Accordingly, other r aspects, advantages, embodiments and modifications are within the scope of the following claims.

What is claimed is:

1. A nanoparticle comprising a rare earth metal fluoride composition according to the formula $M1M2F_4$ wherein $M^1$ is sodium, $M^2$ is the rare earth, and wherein the rare earth metal fluoride composition comprises:
   ytterbium in an amount from about 75 mol % to about 85 mol % of the rare earth present in the composition;
   erbium in an amount from about 1 mol % to about 3 mol % of the rare earth present in the composition; and
   yttrium in an amount from about 15 mol % to about 25 mol % of the rare earth present in the composition;
   and wherein the nanoparticle comprises a layer comprising calcium fluoride coating the rare earth metal fluoride composition.

2. The nanoparticle of claim 1 wherein the rare earth metal fluoride composition comprises:
   ytterbium in an amount of about 80 mol % of the rare earth present in the composition;
   erbium in an amount of about 2 mol % of the rare earth present in the composition; and
   yttrium in an amount of about 18 mol % of the rare earth present in the composition.

3. The nanoparticle of claim 1 further comprising a photosensitizer, or precursor thereof.

4. The nanoparticle of claim 3, wherein the photosensitizer or precursor thereof is covalently attached to the nanoparticle.

5. The nanoparticle of claim 4, wherein the photosensitizer or precursor thereof is 5-aminolevulinic acid.

6. The nanoparticle of claim 3, wherein the photosensitizer or precursor thereof is 5-aminolevulinic acid.

7. The nanoparticle of claim 1 comprising:
the rare earth metal fluoride composition comprising:
ytterbium in an amount of about 80 mol % of the rare earth present in the composition;
erbium in an amount of about 2 mol % of the rare earth present in the composition; and
yttrium in an amount of about 18 mol % of the rare earth present in the composition;
the layer comprising calcium fluoride;
an outer coating comprising polyacrylic acid; and
5-aminolevulinic acid conjugated via an acylhydrazone linkage to the polyacrylic acid.

8. The nanoparticle of claim 1 comprising:
the rare earth metal fluoride composition comprising:
ytterbium in an amount from about 75 to about 85 mol % of the rare earth present in the composition;
erbium in an amount from about 1 to about 3 mol % of the rare earth present in the composition; and
yttrium in an amount from about 15 to about 25 mol % of the rare earth present in the composition;
the layer comprising calcium fluoride;
an outer coating comprising polyacrylic acid; and
5-aminolevulinic acid conjugated an acylhydrazone linkage to the polyacrylic acid.

9. The nanoparticle of claim 1, wherein the nanoparticle is effective to upconvert infrared radiation to produce red fluorescence emission with a wavelength in the range from 625 nm to about 700 nm.

10. The nanoparticle of claim 1, wherein the composition has a cubic structure.

11. A method of treating a tumor in a subject in need of such treatment comprising:
administering to the subject an effective amount of the nanoparticle of claim 4;
and
subsequently administering to the subject an effective amount of infra-red radiation.

12. The method of claim 11, wherein the photosensitizer or precursor thereof is 5-aminolevulinic acid.

13. A method of treating a tumor in a subject in need of such treatment comprising:
administering to the subject an effective amount of the nanoparticle of claim 7; and
subsequently administering to the subject an effective amount of infra-red radiation.

14. A method of treating a tumor in a subject in need of such treatment comprising:
administering to the subject an effective amount of the nanoparticle of claim 8; and
subsequently administering to the subject an effective amount of infra-red radiation.

15. A method of preparing an upconverting nanoparticle comprising reacting in a reaction mixture rare earth trifluoroacetates and sodium trifluoroacetate under conditions sufficient to form a nanoparticle comprising a sodium rare earth tetrafluoride, wherein the rare earth trifluoroacetates comprise:
ytterbium trifluoroacetate in an amount from about 75 mol % to about 85 mol % of the rare earth trifluoroacetates present in the reaction mixture;
erbium trifluoroacetate in an amount from about 1 mol % to about 3 mol % of the rare earth trifluoroacetates present in the reaction mixture; and
yttrium trifluoroacetate in an amount from about 15 mol % to about 25 mol % of the rare earth trifluoroacetates present in the reaction mixture; and
subsequently coating the nanoparticle with a shell comprising calcium fluoride.

16. A method according to claim 15 wherein the rare earth trifluoroacetates consist of:
ytterbium trifluoroacetate in an amount of about 80 mol % of the rare earth trifluoroacetates present in the reaction mixture;
erbium trifluoroacetate in an amount of about 2 mol % of the rare earth trifluoroacetates present in the reaction mixture; and
yttrium trifluoroacetate in an amount of about 18 mol % of the rare earth trifluoroacetates present in the reaction mixture.

17. A nanoparticle prepared according to the method of claim 15.

18. A nanoparticle prepared according to the method of claim 16.

* * * * *

UNITED STATES PATENT AND TRADEMARK OFFICE
CERTIFICATE OF CORRECTION

PATENT NO.         : 9,956,426 B2                                    Page 1 of 1
APPLICATION NO.    : 14/632752
DATED              : May 1, 2018
INVENTOR(S)        : Amol Punjabi It is certified that error appears in the above-identified patent and that said Letters Patent is hereby corrected as shown below:

On the Title Page

Column 1, Line 3, after "0 days." delete "days.".

In the Claims

Column 32, Line 46, Claim 1, delete "M1M2F$_4$" and insert -- $M^1M^2F_4$ --, therefor.

Signed and Sealed this
Eleventh Day of December, 2018

Andrei Iancu
*Director of the United States Patent and Trademark Office*